US012364982B2

United States Patent
Wheeler et al.

(10) Patent No.: US 12,364,982 B2
(45) Date of Patent: Jul. 22, 2025

(54) SYSTEM FOR IDENTIFYING AND TARGETING INDIVIDUAL CELLS WITHIN A HETEROGENEOUS POPULATION FOR SELECTIVE EXTRACTION OF CELLULAR CONTENT

(71) Applicant: THE GOVERNING COUNCIL OF THE UNIVERSITY OF TORONTO, Toronto (CA)

(72) Inventors: Aaron Ray Wheeler, Toronto (CA); Michael Dean Chamberlain, Toronto (CA); Julian Lucas Lamanna, Toronto (CA); Michael David Murdoch Dryden, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 905 days.

(21) Appl. No.: 16/370,414

(22) Filed: Mar. 29, 2019

(65) Prior Publication Data

US 2019/0224678 A1 Jul. 25, 2019

Related U.S. Application Data

(63) Continuation of application No. 16/338,306, filed as application No. PCT/CA2017/051158 on Sep. 29, 2017, now abandoned.

(Continued)

(51) Int. Cl.
*B01L 3/00* (2006.01)
*C12M 1/33* (2006.01)
(Continued)

(52) U.S. Cl.
CPC ... *B01L 3/502753* (2013.01); *B01L 3/502715* (2013.01); *C12M 1/33* (2013.01);
(Continued)

(58) Field of Classification Search
CPC ......... B01L 3/502753; B01L 3/502715; B01L 3/502761; B01L 2200/0668;
(Continued)

(56) References Cited

U.S. PATENT DOCUMENTS 6,156,576 A    12/2000  Allbritton et al.
7,815,871 B2 * 10/2010  Pamula ............. B01L 3/502792
                                                                422/81

(Continued)

FOREIGN PATENT DOCUMENTS

CN      101583722 A    11/2009
CN      102341505 A     2/2012
(Continued)

OTHER PUBLICATIONS

Srinivasan et al. "An Integrated digital microfluidic lab-on-a-chip for clinical diagnostics on human physiological fluids," Lab Chip, 2004, 4, 310-315 (Year: 2004).*

(Continued)

*Primary Examiner* — Neil N Turk

(57) ABSTRACT

A system for identifying and targeting individual cells within a cell population for selective extraction of cellular content. The system includes a digital microfluidic device having at least one hydrophilic site for receiving cells, an imaging system including a stage for receiving the digital microfluidic device and an imaging module for identifying at least one targeted cell among the cells at the at least one hydrophilic site and a pulsed laser source for lysing the targeted cell to produce a lysate. A control system controls the pulsed laser source, the imaging system and the digital (Continued)

microfluidic device and is programmed for coordinating steps of i) moving droplets on the digital microfluidic device, ii) selecting the targeted cell to be lysed located at the hydrophilic site, iii) illuminating the selected targeted cell by the pulsed laser source to lyse the selected targeted cell to produce lysate, and iv) collecting the lysate.

28 Claims, 17 Drawing Sheets

Related U.S. Application Data

(60) Provisional application No. 62/402,208, filed on Sep. 30, 2016.

(51) Int. Cl.
| | |
|---|---|
| C12M 1/34 | (2006.01) |
| C12M 1/42 | (2006.01) |
| C12N 1/06 | (2006.01) |
| C12Q 1/6806 | (2018.01) |
| C12Q 1/6881 | (2018.01) |
| G01N 1/28 | (2006.01) |
| G01N 15/00 | (2006.01) |
| G01N 15/10 | (2024.01) |
| G01N 15/14 | (2006.01) |
| G01N 35/00 | (2006.01) |
| B01L 7/00 | (2006.01) |
| G01N 1/40 | (2006.01) |
| G01N 15/149 | (2024.01) |
| G01N 33/50 | (2006.01) |

(52) U.S. Cl.
CPC .............. *C12M 1/34* (2013.01); *C12M 1/42* (2013.01); *C12N 1/066* (2013.01); *C12Q 1/6806* (2013.01); *C12Q 1/6881* (2013.01); *G01N 1/28* (2013.01); *G01N 15/00* (2013.01); *G01N 15/10* (2013.01); *G01N 15/1468* (2013.01); *G01N 35/00* (2013.01); *B01L 3/502761* (2013.01); *B01L 3/502792* (2013.01); *B01L 7/52* (2013.01); *B01L 2200/0647* (2013.01); *B01L 2200/0668* (2013.01); *B01L 2300/0867* (2013.01); *B01L 2300/089* (2013.01); *B01L 2400/0421* (2013.01); *B01L 2400/0442* (2013.01); *C12Q 2565/629* (2013.01); *G01N 1/286* (2013.01); *G01N 1/40* (2013.01); *G01N 2015/1006* (2013.01); *G01N 2015/1028* (2024.01); *G01N 15/149* (2024.01); *G01N 33/5005* (2013.01)

(58) Field of Classification Search
CPC ....... B01L 3/502792; B01L 2400/0442; B01L 2300/089; B01L 2300/0867; B01L 2400/0421; B01L 7/52; B01L 2200/0647; G01N 15/00; G01N 35/00; G01N 1/28; G01N 15/1468; G01N 15/10; G01N 2015/149; G01N 1/286; G01N 2015/1006; G01N 1/40; G01N 2015/1081; C12M 1/34; C12M 1/42; C12M 1/33; C12N 1/066; C12Q 1/6806; C12Q 1/6881; C12Q 2565/629
See application file for complete search history.

(56) References Cited

U.S. PATENT DOCUMENTS

| | | | |
|---|---|---|---|
| 2001/0005586 A1 | 6/2001 | Palsson et al. | |
| 2004/0058423 A1 | 3/2004 | Albritton et al. | |
| 2004/0058450 A1* | 3/2004 | Pamula | B01L 3/502792 |
| | | | 436/52 |
| 2004/0126818 A1 | 7/2004 | Chan-Hui et al. | |
| 2006/0223178 A1 | 10/2006 | Barber et al. | |
| 2009/0203063 A1 | 8/2009 | Wheeler et al. | |
| 2010/0015614 A1* | 1/2010 | Beer | B01L 3/502792 |
| | | | 435/6.12 |
| 2011/0059556 A1* | 3/2011 | Strey | G01N 33/54326 |
| | | | 422/503 |
| 2013/0168250 A1 | 7/2013 | Fogleman et al. | |
| 2014/0061049 A1* | 3/2014 | Lo | G01N 27/44704 |
| | | | 204/547 |
| 2014/0199719 A1 | 7/2014 | Shih et al. | |
| 2014/0212881 A1* | 7/2014 | Handique | C12Q 1/6841 |
| | | | 435/6.12 |

FOREIGN PATENT DOCUMENTS

| | | |
|---|---|---|
| CN | 104350374 A | 2/2015 |
| CN | 105408728 A | 3/2016 |
| WO | 99/45372 A1 | 9/1999 |
| WO | 2008008515 A2 | 1/2008 |
| WO | 2009100516 A1 | 8/2009 |
| WO | 2010081052 A1 | 7/2010 |
| WO | 2012037308 | 3/2012 |
| WO | 2013130714 A1 | 9/2013 |
| WO | 2015023747 A | 2/2015 |
| WO | 2010016916 | 11/2019 |

OTHER PUBLICATIONS

Brown et al. "Sampling Efficiency of a Single-Cell Capillary Electrophoresis System" Cytometry Part A 71A: 882-888, 2007 (Year: 2007).*
Lai et al. "Characterization and use of laser-based lysis for cell analysis on-chip" J. R. Soc. Interface (2008) 5, S113-S121 (Year: 2008).*
Sims et al. "Laser-Micropipet Combination for Single-Cell Analysis", Anal. Chem. 1998, 70, 4570-4577 (Year: 1998).*
Fan et al. "Microfluidic digital PCR enables rapid prenatal diagnosis of fetal aneuploidy", American Journal of Obstetrics and Gynecology vol. 200, Issue 5, May 2009, pp. 543.e1-543.e7 (Year: 2009).*
Salehi-Reyhani et al. "A first step towards practical single cell proteomics: a microfluidic antibody capture chip with TIRF detection" Lab Chip, 2011, 11, 1256, (Year: 2011).*
Xie et al. "Automated Translational and Rotational Control of Biological Cells With a Robot-Aided Optical Tweezers Manipulation System" IEEE Transactions on Automation Science and Engineering, vol. 13, No. 2, Apr. 2016 (Year: 2016).*
Dickinson et al. "Automated Capillary Electrophoresis System for Fast Single-Cell Analysis" Anal. Chem. 2013, 85, 4797-4804 (Year: 2013).*
Jen et al. "Single-Cell Chemical Lysis on Microfluidic Chips with Arrays of Microwells" Sensors 2012, 12, 347-358 (Year: 2012).*
He et al. "Selective encapsulation of single cells and subcellular organelles into picoliter and femtoliter-volume droplets," Analytical Chem. 2005, vol. 77, pp. 1539-1544 (Year: 2005).*
Lai et al. "Characterization and use of laser-based lysis for cell analysis on-chip," J. R. Sc. Interface, 2008, vol. 5, S113-S121 (Year : 2008).*
K. Scott Phillips et al: "Air-stable supported membranes for single-cell cytometry on PDMS microchips", Lab on a Chip, vol. 10, No. 7, Jan. 1, 2010 , p. 864, XP055729167.
Alphonsus H.C. Ng et al: "Digital Microfluidic Cell Culture", Annual Review of Biomedical Engineering vol. 17, No. 1, Dec. 7, 2015 (Dec. 7, 2015), pp. 91-112.
He M et al: "Selective encapsulation of single cells and subcellular organelles into picoliter-and femtoliter-volume droplets", Analytical Chemistry, American Chemical Society, US, vol. 77, No. 6, Mar. 15, 2005 (Mar. 15, 2005), pp. 1539-1544.
K. Scott Phillips et al: "Continuous analysis of dye-loaded, single cells on a microfluidic chip", Lab on a Chip, vol. 11, No. 7, Apr. 7, 2011 (Apr. 7, 2011), p. 1333.

(56) References Cited

OTHER PUBLICATIONS

Ali Salehi-Reyhani et al: "Chemical-Free Lysis and Fractionation of Cells by Use of Surface Acoustic Waves for Sensitive Protein Assays", Analytical Chemistry, vol. 87, No. 4, Jan. 26, 2015, pp. 2161-2169.
Darius G. Rackus et al: "A digital microfluidic device with integrated nanostructured microelectrodes for electrochemical immunoassays", Lab on a Chip, vol. 15, No. 18, Jan. 1, 2015, pp. 3776-3784.
Communication pursuant to Article 94(3) EPC issued by the European Patent Office on Aug. 29, 2024, in the corresponding European Patent Application No. 20176237.4.
Brown and Audet, "Current techniques for single-cell lysis", J. R. Soc. Interface, Apr. 15, 2008, pp. S131-S138, vol. 5, The Royal Society.
Alphonsus H.C. Ng, et al. Digital microfluidic immunocytochemistry in single cells. Nature Communications, Jun. 24, 2015. 6: p. 7513.
Tang, D.G., Understanding cancer stem cell heterogeneity and plasticity. Cell Res, 2012. 22(3): p. 457-472.
Graf, T. and M. Stadtfeld, Heterogeneity of embryonic and adult stem cells. Cell Stem Cell, 2008. 3(5): p. 480-483.
Lecault, V., et al., High-throughput analysis of single hematopoietic stem cell proliferation in microfluidic cell culture arrays. Nat Methods, 2011. 8(7): p. 581-586.
Macaulay, I.C., et al., G&T-seq: parallel sequencing of single-cell genomes and transcriptomes. Nat Methods, 2015. 12(6): p. 519-522.
Macaulay, I.C. and T. Voet, Single cell genomics: advances and future perspectives. PLoS Genet, 2014. 10(1): p. e1004126.
Macosko, Evan Z., et al., Highly Parallel Genome-wide Expression Profiling of Individual Cells Using Nanoliter Droplets. Cell, 2015. 161(5): p. 1202-1214.
Treutlein, B., et al., Reconstructing lineage hierarchies of the distal lung epithelium using single-cell RNA-seq. Nature, 2014. 509(7500): p. 371-375.
Kolodziejczyk, A.A., et al., The technology and biology of single-cell RNA sequencing. Mol Cell, 2015. 58(4): p. 610-620.
Klein, A.M., et al., Droplet barcoding for single-cell transcriptomics applied to embryonic stem cells. Cell, 2015. 161(5): p. 1187-1201.
Ng, A.H., et al., Digital microfluidic magnetic separation for particle-based immunoassays. Anal Chem, 2012. 84(20): p. 8805-8812.
Ng, A.H., et al., Digital microfluidic platform for the detection of rubella infection and immunity: a proof of concept. Clin Chem, 2015. 61(2): p. 420-429.
Barbulovic-Nad, I., S.H. Au, and A.R. Wheeler, A microfluidic platform for complete mammalian cell culture. Lab Chip, 2010. 10(12): p. 1536-1542.
Srigunapalan, S., et al., A digital microfluidic platform for primary cell culture and analysis. Lab Chip, 2012. 12(2): p. 369-375.
Lecault, V., et al., Microfluidic single cell analysis: from promise to practice. Curr Opin Chem Biol, 2012. 16(3-4): p. 381-390.
Lai, H.H., et al., Characterization and use of laser-based lysis for cell analysis on-chip. J R Soc Interface, 2008. 5 Suppl 2: p. S113-S121.
Quinto-Su, P.A., et al., Examination of laser microbeam cell lysis in a PDMS microfluidic channel using time-resolved imaging. Lab Chip, 2008. 8(3): p. 408-414.
Sims, C.E., et al., Laser-micropipet combination for single-cell analysis. Anal Chem, 1998. 70(21): p. 4570-4577.
Eydelnant, I.A., et al., Virtual microwells for digital microfluidic reagent dispensing and cell culture. Lab Chip, 2012. 12(4): p. 750-757.
Kratschmer, E, et al., Image processing using shape recognition for alignment to damaged registration marks in electron beam lithography. J. Vac. Sci. Technol., B: Microelectron. Nanometer Struct.—Process., Meas., Phenom. B, 2009. 27: p. 2563-2568.
Held, M and Karp, RM, A Dynamic Programming Approach to Sequencing Problems. J. Soc. Ind. Appl. Math. 1962 10(1): p. 196-210.
Johnson, D. S.; McGeoch, L. A. (1997). "The Traveling Salesman Problem: A Case Study in Local Optimization". In Aarts, E. H. L.; Lenstra, J. K. Local Search in Combinatorial Optimisation. London: John Wiley and Sons Ltd. pp. 215-310.
International Search Report, PCT/CA2017/051158, dated Jan. 11, 2018.

\* cited by examiner

A

B

CVS Control

Laser Lysis

C

SYSTEM FOR IDENTIFYING AND TARGETING INDIVIDUAL CELLS WITHIN A HETEROGENEOUS POPULATION FOR SELECTIVE EXTRACTION OF CELLULAR CONTENT

FIELD

Devices for use in identifying and targeting individual cells for lysis in a heterogeneous cell environment, said cell lysates being subject to further downstream analysis. Also provided are methods of using the devices as well as systems and kits that comprise the devices. The devices, systems, methods and kits find use in a variety of different applications, including testing and diagnostics.

BACKGROUND

In the last decade it has become clear that cell populations that were thought to be the same can actually be very heterogeneous in nature. Two examples of this are (a) the population of cancer cells that make up a tumour, and (b) stem cells and their progeny. There is great interest in having methods to identify and study individual cells or small subpopulations of cells in complex mixtures. In addition, with the discovery of the existence of rare cell populations (e.g., cancer cells or immune cells in blood, fetal cells in maternal samples, etc.), there is great interest in the development of methods to isolate and characterize individual cells.

Single-cell genomic analysis relying on flow cytometry or microchannel-based sorting has been previously investigated [3-10] and the Polaris™ system was commercially released for this purpose. The use of flow cytometry-based or microchannel-based sorting for single cell genomic analysis is quite useful for various applications, however, the use of these technologies is limited to the analysis of suspensions of cells in liquid media. Furthermore devices using these technologies are limited in the number of cells that can be evaluated at the same time.

Microfluidics regards miniaturized fluid-handling technologies for processing or manipulating extremely small volumes of fluids. Such technologies include digital microfluidics (DMF) (sometimes also known as "electrowetting" or "electrowetting-on-dielectric") which relies on fluid manipulated as droplets on an open array (with no channels), and integrated fluidic circuits (ITC) which relies on fluid pumped through enclosed micron-dimension channels. The integration of laser microbeam cell lysis with ITCs (in enclosed micron dimension channels) has been previously reported. Quinto-Su described a number of challenges using such approach, including the tendency of plasma-induced bubbles to clog, deform, or damage the microchannels, making the method impractical for regular use [17]. Lai reported that some of these problems may be corrected by focusing the laser microbeam to a smaller spot [16]. However, downstream analysis was limited perhaps because of cell lysate dilution in the microchannel.

SUMMARY

Disclosed herein is a system for identifying and targeting individual cells within a cell population for selective extraction of cellular content, comprising:
a digital microfluidic device having at least one site for receiving cells;
an imaging system including a stage for receiving the digital microfluidic device, the imaging system including an imaging module for identifying at least one targeted cell among the cells at the at least one site and a pulsed laser source for laser lysing the at least one targeted cell thereby releasing the cell content to produce a lysate; and
a control system for controlling the pulsed laser source, the imaging system and the digital microfluidic device, the control system being programmed with instructions for coordinating steps of
moving of droplets on the digital microfluidic device,
selecting of the at least one targeted cell to be lysed located at the at least one site,
illuminating of the at least one selected targeted cell by the pulsed laser source to lyse the at least one selected targeted cell to produce lysate, and
collecting of the lysate.

The at least one site may be hydrophilic, partially hydrophilic or become hydrophilic after protein fouling/adsorption from the sample.

The digital microfluidic device may include a top plate and a bottom plate defining a space there between, and wherein each of the at least one site has an external perimeter, each of the at least one site being defined on a surface of at least one of the plates for forming a corresponding virtual microwell, each corresponding virtual microwell having a virtual wall extending from the external perimeter of the site between the top and bottom plates, and upon illumination of the at least one selected targeted cell by the pulsed laser source, a plasma bubble is formed in the virtual microwell, and upon formation of the plasma bubble, the virtual wall deforms thereby absorbing energy released by the expanding plasma bubble.

The at least one site may be a plurality of sites, and wherein the control system is programmed with instructions for coordinating
moving of droplets to the plurality of sites,
selecting at least one cell to be lysed at each of the plurality of sites,
selecting a first site to illuminate with the pulsed laser source the at least one selected cell at that site,
moving of the stage to move the digital microfluidic device sequentially from the first site to another site to bring each of the sites into a field of view of the pulsed laser source to lyse the at least one selected cell to produce lysate at each site, and
collecting the lysate at each site.

In this aspect the control system may be programmed for calculating a shortest distance travelled by the stage to bring sequentially each of the plurality of sites into the field of view of the pulsed laser.

The at least one selected targeted cell may be a plurality of selected targeted cells with the control system being programmed for
identifying a sequence of selected targeted cells to be lysed to minimize a time to perform the coordinating steps, and
wherein the plurality of selected targeted cells is within one field of view, or a plurality of field of views, or within a plurality of sites.

In this aspect the sequence of selected targeted cells is based on a shortest path between the plurality of selected targeted cells.

The imaging system may include a translation mechanism for displacement of the stage, the translation mechanism being controlled by the control system.

The control system may include a droplet control mechanism or system for controlling displacement of droplets of fluid from a fluid reservoir towards the at least one site.

The pulsed laser source may be a nanosecond-pulsed laser.

The pulsed laser source may be a nanosecond-pulsed laser delivering pulses of at least 1 µJ.

The pulsed laser source may be a Q-switched laser.

The nanosecond-pulsed laser may be a Nd-based laser.

The nanosecond-pulsed laser may be selected to produce a pulsed-laser beam within the visible spectrum.

The present disclosure also provides a method for identifying and targeting individual cells within a cell population for selective extraction of cellular content, comprising:
    loading a sample containing cells on at least one site of a digital microfluidic device thereby forming a virtual microwell at each of the at least one site;
    Immobilizing the cells on the at least one site;
    selecting at least one immobilized cell;
    lysing the at least one selected cell using a pulsed laser source to produce lysate within its corresponding virtual microwell;
    displacing a droplet of liquid to the corresponding virtual microwell for collecting the lysate; and
    moving the droplet containing the lysate from the corresponding virtual microwell to a designated site.

The at least one site is hydrophilic, partially hydrophilic or become hydrophilic after protein fouling/adsorption from the sample.

The method may further include a step of generating a map of locations of the immobilized cells, and wherein the step of selecting the at least one immobillized cell includes selecting the at least one cell from the map.

The method may further comprise a step of labelling the immobilized cells. This step of labelling the immobilized cells may further comprise fixing the cells.

The method may further comprise steps of:
    moving the digital microfluidic device along horizontal axes and a vertical axis for positioning the digital microfluidic device for lysing another at least one selected cell from immobilized cells;
    lysing the other at least one selected cell using the pulsed laser source to produce another lysate within its corresponding virtual microwell;
    displacing another droplet of liquid to the corresponding virtual microwell for collecting the other lysate; and
    moving the other droplet containing the other lysate from the corresponding virtual microwell to a designated site.

The method further comprise a step of introducing the sample containing the cells at an initial site and displacing the sample to the at least one site.

The at least one site is a plurality of sites, and including steps of
    moving of droplets to said plurality of sites,
    selecting of a cells to be lysed at each of said plurality of sites,
    selecting a first site to illuminate the selected cell at that site,
    moving of the stage to move the digital microfluidic device sequentially to bring each of the sites into a field of view of the pulsed laser source to lyse the selected cell to produce lysate at each site, and
    collecting the lysate at each site.

In this aspect the method may include calculating a shortest distance travelled by the stage to bring each of the plurality of sites into the field of view of the pulsed laser source sequentially.

The at least one selected targeted cell may a plurality of selected targeted cells, and the method may further include
    identifying a sequence of selected targeted cells to be lysed to minimize a time to perform the lysing on all selected targeted cells, and wherein the plurality of selected targeted cells is within one field of view, or a plurality of field of views, or within a plurality of sites.

In the method the pulsed laser source may be a nanosecond-pulsed laser.

In the method the pulsed laser source may be a nanosecond-pulsed laser delivering pulses of at least 1 µJ.

In the method the nanosecond-pulsed laser may be a Nd-based laser.

The nanosecond-pulsed laser may be selected to produce a pulsed-laser beam within the visible spectrum.

The pulsed laser source may be a Q-switched laser.

The method may further comprise the step of performing on chip analysis of the lysate at the designated site, and may further comprise the step of collecting the droplet containing the lysate from the designated site for off-chip analysis.

The method may be used in the case there the individual cells are fetal cells, and may be configured for prenatal genetic testing or screening, or detection or diagnosis of a prenatal condition.

Also disclosed herein is method for detection and/or isolation of fetal cells and/or fetal analytes, the method comprising:
    loading a sample containing cells on at least one site of a digital microfluidic device thereby forming a virtual microwell at each of the at least one site;
    immobilizing the cells on the at least one site;
    selecting at least one immobilized fetal cell;
    lysing the at least one selected cell using a pulsed laser source to produce lysate within its corresponding virtual microwell;
    displacing a droplet of liquid to the corresponding virtual microwell for collecting the lysate; and
    moving the droplet containing the lysate from the corresponding virtual microwell to a designated site, and optionally detecting and/or isolating fetal analytes in the lysate.

BRIEF DESCRIPTION OF DRAWINGS

Embodiments will now be described, by way of example only, with reference to the drawings, in which.

DETAILED DESCRIPTION

Figure 1:
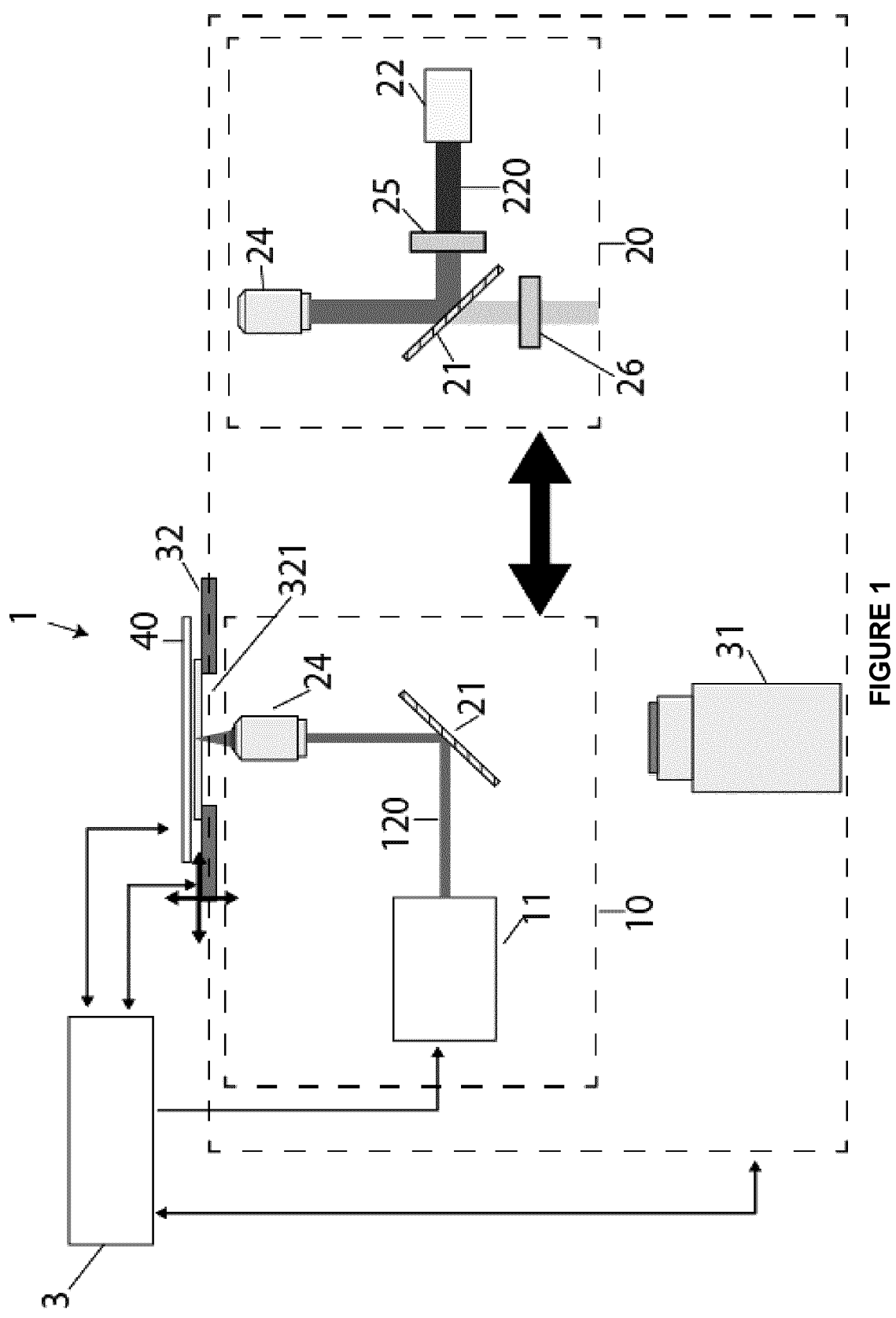
FIG. 1 is a schematic diagram of a system for identifying and targeting individual cells within a cell population for selective extraction of cellular content according to an embodiment of the present disclosure.

Various embodiments and aspects of the disclosure will be described with reference to details discussed below. The following description and drawings are illustrative of the disclosure and are not to be construed as limiting the disclosure. The figures are not to scale. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary", "illustrative" and "for example" mean "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art.

According to an embodiment, the present invention provides a system for identifying and targeting individual cells within a cell population for selective extraction of cellular content. According to another embodiment, the present invention provides a system for identifying and targeting individual adherent cells within a heterogeneous cell population for selective extraction of cellular content. The system may comprise a DMF device and an imaging system having a lysis module and an imaging module.

According to an embodiment, the present invention provides a method for identifying and targeting individual cells within a cell population for selective extraction of cellular content using a system comprising a DMF device and an imaging system having a lysis module and an imaging module. According to another embodiment, a method for identifying and targeting individual adherent cells within a heterogeneous cell population for selective extraction of cellular content is also provided. The method may use a system comprising a DMF device and an imaging system having a lysis module and an imaging module. The adherent cell samples may be introduced onto a DMF device, where they may be cultured and interrogated using microfluidic immunocytochemistry. Cells of interest may be identified and selected and their content extracted selectively by laser microbeam lysis. The selected cell lysate contents may be collected into droplets which may be analyzed on-chip or off-chip.

In an embodiment there is provided a system for identifying and targeting individual cells within a cell population for selective extraction of cellular content. The system includes a digital microfluidic device having at least one site for receiving cells and an imaging system including a stage for receiving the digital microfluidic device, the imaging system including an imaging module for identifying at least one targeted cell among the cells at the at least one site and a pulsed laser source for laser lysing the at least one targeted cell thereby releasing the cell content to produce a lysate. The system includes a control system for controlling the pulsed laser source, the imaging system and the digital microfluidic device. The control system is programmed with instructions for coordinating steps of moving of droplets on the digital microfluidic device, selecting of the at least one targeted cell to be lysed located at the at least one site, illuminating of the at least one selected targeted cell by the pulsed laser source to lyse the at least one selected targeted cell to produce lysate, and collecting of the lysate.

In some embodiments the at least one site for receiving cells may be hydrophilic, partially hydrophilic or become hydrophilic after protein fouling/adsorption from the sample.

In an embodiment the digital microfluidic device may include a top plate and a bottom plate defining a space there between, and wherein each of the at least one site has an external perimeter, each of the at least one site being defined on a surface of at least one of the plates for forming a corresponding virtual microwell, each corresponding virtual microwell having a virtual wall extending from the external perimeter of the site between the top and bottom plates. Upon illumination of the at least one selected targeted cell by the pulsed laser source, a plasma bubble is formed in the virtual microwell, and upon formation of the plasma bubble, the virtual wall deforms thereby absorbing energy released by the expanding plasma bubble.

In an embodiment the at least one sites is a plurality of sites, and wherein the control system is programmed with instructions for coordinating
  moving of droplets to said plurality of sites,
  selecting at least one cell to be lysed at each of said plurality of sites,
  selecting a first site to illuminate with the pulsed laser source the at least one selected cell at that site,
  moving of the stage to move the digital microfluidic device sequentially from the first site to another site to bring each of the sites into a field of view of the pulsed laser source to lyse the at least one selected cell to produce lysate at each site, and
  collecting the lysate at each site.

In the embodiment having a plurality of sites, the control system may be programmed for calculating a shortest distance travelled by the stage to bring sequentially each of the plurality of sites into the field of view of the pulsed laser.

In an embodiment the at least one selected targeted cell is a plurality of selected targeted cells, and the control system may be programmed for
  identifying a sequence of selected targeted cells to be lysed to minimize a time to perform the coordinating steps, and
  wherein the plurality of selected targeted cells is within one field of view, or a plurality of field of views, or within a plurality of sites.

The sequence of selected targeted cells may be based on a shortest path between the plurality of selected targeted cells.

In an embodiment the imaging system may include a translation mechanism for displacement of the stage, the translation mechanism being controlled by the control system.

In an embodiment the control system may include a droplet control means for controlling displacement of droplets of fluid from a fluid reservoir towards the at least one site.

In an embodiment the pulsed laser source is a nanosecond-pulsed laser.

In an embodiment the pulsed laser source may be a nanosecond-pulsed laser delivering pulses of at least 1 µJ.

In an embodiment the nanosecond-pulsed laser may be a Nd-based laser.

In an embodiment the nanosecond-pulsed laser produces a pulsed-laser beam within the visible spectrum.

In an embodiment the pulsed laser source may be a Q-switched laser.

According to an embodiment, referring to FIG. 1, a system for identifying and targeting individual cells within a cell population for selective extraction of cellular contents 1 may comprise a DMF device 40 and an imaging system 30.

The imaging system 30 may be equipped with a lysis module 10 and an imaging module 20. The imaging system 30 may be any suitable optical imaging system known in the art that can capture brightfield and fluorescent images and that may direct a laser beam into a focused laser beam for forming a plasma bubble at the same plane of imaging. According to an embodiment, the imaging system 30 may be a microscope such as an inverted microscope. The imaging system 30 may have a motorized stage 32 for cell localization, image tilting and autofocusing and an optical unit 31 configured for both brightfield and fluorescent imaging. One possible but not limiting example of the inverted microscope is an Olympus IX-71 series model. According to another embodiment, the imaging system, instead of being equipped with the motorized stage 32, may have a fixed stage and motorized lens and mirrors for cell localization, image tiling and autofocusing.

The lysis module 10 may comprise a pulsed laser source 11 which emits a laser microbeam 120. The pulsed laser source 11 is aligned using a dichroic mirror 21 into the magnification objective lens 24 and the opening 321 of the motorized stage 32. The pulsed laser source 11 may be a laser source capable of producing a high-energy pulsed laser beam. According to an embodiment, the pulsed laser source 11 may be a nanosecond-pulsed laser delivering pulses of at least 1 µJ. According to another embodiment, the pulsed laser source 11 may be a nanosecond-pulsed laser delivering pulses of >4-6 µJ and able to produce pulses of approximately 0.5 to 50 ns or a faster laser such as an ultrafast laser (femtosecond-pulsed laser or picosecond-pulsed laser). The pulsed laser source 11 may be a Q-switched laser, gain-switched laser, mode-locked laser or a pulsed-pumped laser. According to another embodiment, the pulsed laser source 11 may be able to emit a pulsed laser beam within the visible spectrum. More particularly, the pulsed laser source 11 may be a Nd-based laser, e.g., a 532 nm Q-switched Nd:YAG laser. According to an embodiment, the nanosecond-pulsed laser may produce a pulsed-laser beam within the visible spectrum.

The imaging module 20 may comprise a light source 22 which emits a light beam 220. The light source 22 may be aligned using a dichroic mirror 21 into the magnification objective lens 24 and the opening 321 of the motorized stage 32. The imaging module may further comprise an excitation filter 25 and an emission filter 26.

Figure 2:
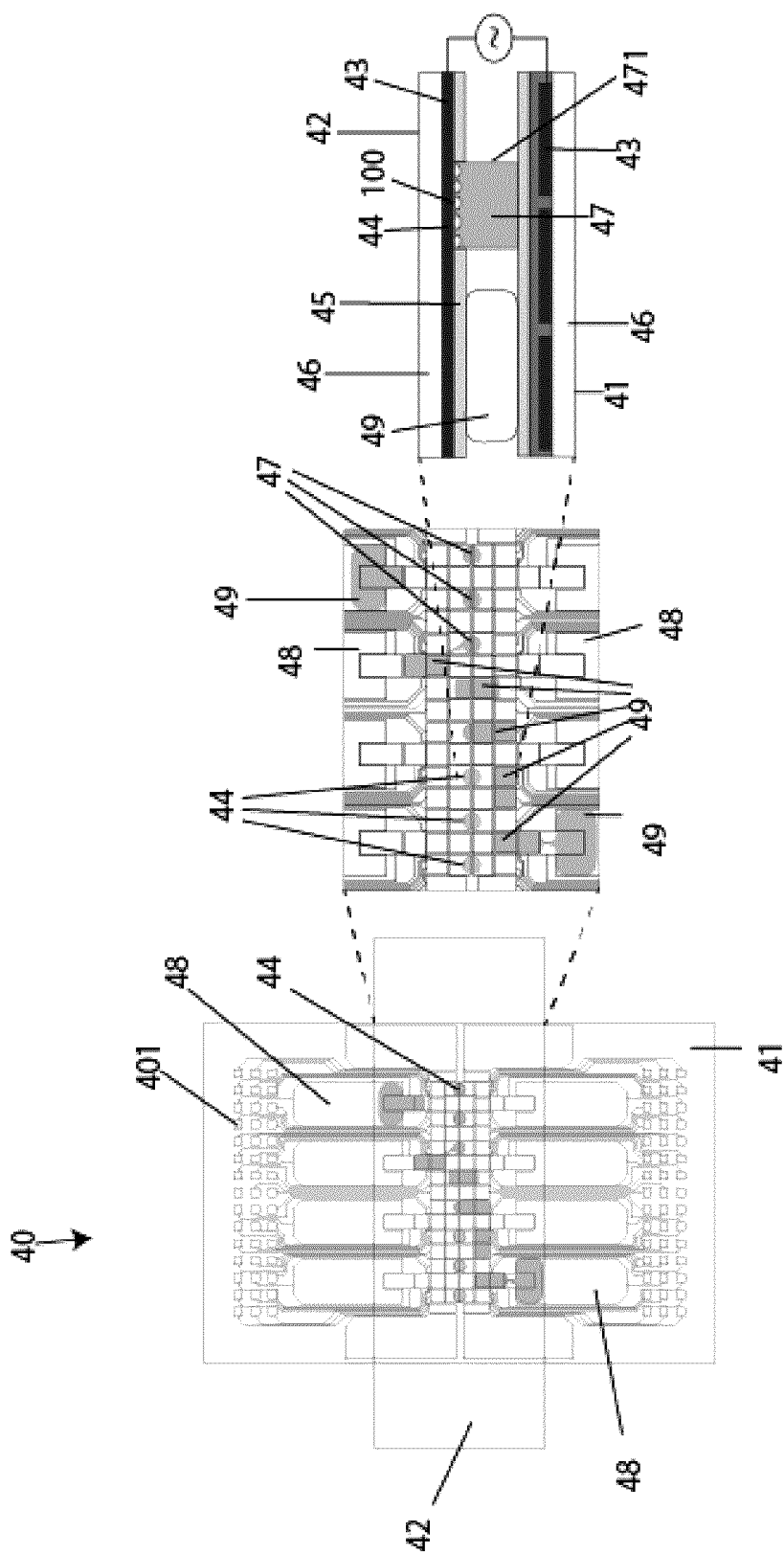
FIG. 2 shows A) a schematic of an assembled DMF device for a cell culture, B) an enlarged portion of the assemble DMF device showing an array of electrodes and hydrophilic sites for passive and active dispensing, and C) a side view of the enlarged portion of the assembled DMF device according to an embodiment of the present disclosure.

The system 1 may further comprise a control system 3 which may allow the coordinated management of the droplet manipulation and lysis of the targeted cells. The motorized stage 32 may be configured to be controlled by the control system 3 to program and manage droplet movement on the DMF device 40. For example the motorized stage 32 may be modified with an array of pogo pins 401 that allow the control system 3 to control the droplet movement as shown in FIG. 2.

According to another embodiment, the control system 3 may comprise a droplet control system or mechanism, a computer and a control board. An example of such a system is the open source "DropBot" system (described at http://microfluidics.utoronto.ca/dropbot/) which may be controlled centrally via a computer and control board, allowing for the coordinated management of droplet manipulation and lysis of targeted cells. The motorized stage 32 may be configured to be controlled by the droplet control system to program and manage droplet movement on the DMF device 40. For example the motorized stage 32 may be modified with an array of pogo pins 401 that allow the control board through the interface of the droplet control system to control the droplet movement.

The DMF device 40 may rest upon the motorized stage 32 which is designed to move laterally to reposition the targeted cells and vertically to focus on a selected targeted cell.

DMF is a fluid handling technology in which sample and reagents are manipulated as discrete droplets on a hydrophobic surface. DMF systems actuate droplets through the application of electrical potentials on a generic array of insulated electrodes. This format enables software-reconfigurable, concurrent droplet operations including merging, mixing, splitting and metering from reservoirs. Complex multi-step procedures can be performed on DMF devices such as DMF device 40, e.g., integrated multiplexed ELISA, long-term multigenerational cell culture and immunocytochemistry. A DMF-based immunocytochemistry method has the advantage of providing the possibility of evaluating adherent cells in situ.

As shown in FIG. 2, the DMF device 40 may be a two-plate DMF device comprising a bottom plate 41 and a top plate 42. The bottom plate 41 may comprise a glass or plastic substrate 46 patterned with electrodes 43 which are coated with a dielectric material 431 and a hydrophobic material 45. The top plate 42 may comprise a glass or plastic substrate 46 coated with a conductive layer, i.e., electrodes 43, which is pattern-coated with the hydrophobic material 45. The patterned coating may be such that the top plate 42 includes patterned hydrophilic sites 44. Both dielectric material 431 and hydrophobic material 45 may be any suitable dielectric material and hydrophobic material known to those skilled in the art respectively, e.g., Parylene™ C for dielectric material 431 and Teflon™ AF for the hydrophobic material 45. Reservoirs 48 are located at both extremities of the bottom plate 41. Droplets 49, which may contain reagents or samples, may be displaced on the DMF device 40 from or to the reservoirs 48 either through active dispensing or passive dispensing. Active dispensing is achieved by actuating electrodes 43 to electrostatically stretch, neck, and pinch a droplet 49. This active dispensing renders possible the reliable and precisely on-demand dispensing at the microliter scale of cell samples and reagents. Passive dispensing is implemented by taking advantage of variations in surface energy on the surface of the DMF device 40 that is primarily hydrophobic but patterned with hydrophilic regions. Passive dispensing occurs spontaneously as a droplet 49 is translated across the hydrophilic site 44. When the droplet 49 is translated across the hydrophilic site 44, surface tension effects result in spontaneous formation of a sub-droplet on the site. Passive dispensing is particularly useful for adherent mammalian cell cultures, allowing for cell 100 seeding onto dry hydrophilic sites 44, as well as for subsequent media and/or reagent exchange on droplet-bearing sites 44. One advantage of passive dispensing is the formation of virtual micro-wells 47 at the hydrophilic sites 44. Virtual microwells 47 are not confined on the sides like traditional wells, but are defined by the surface properties of the bottom and top and plates 41 and 42 and virtual vertical wall 471, which is simply defined by the air-liquid interface of the droplet 49 that is held in place at the hydrophilic site 44 by surface tension of the liquid (see [19] Eydelnant et al. (2012) Lab Chip 12(4):750-757). The volume of the virtual micro-wells 47 is dictated by the diameter of the hydrophilic sites 44 and the distance between bottom 41 and top plates 42. According to an embodiment, the site 44 may be hydrophilic, partially hydrophilic or become hydrophilic after protein fouling/adsorption from the sample.

As shown in FIG. 2, cells 100 from a sample to be analyzed reside between the bottom plate 41 and top plate 42 of the DMF device 40. As the cells 100 cannot grow on a hydrophobic material, the cells 100 are cultured on the hydrophilic sites 44 of the top plate 42 and in the virtual microwell 47.

Figure 3A:
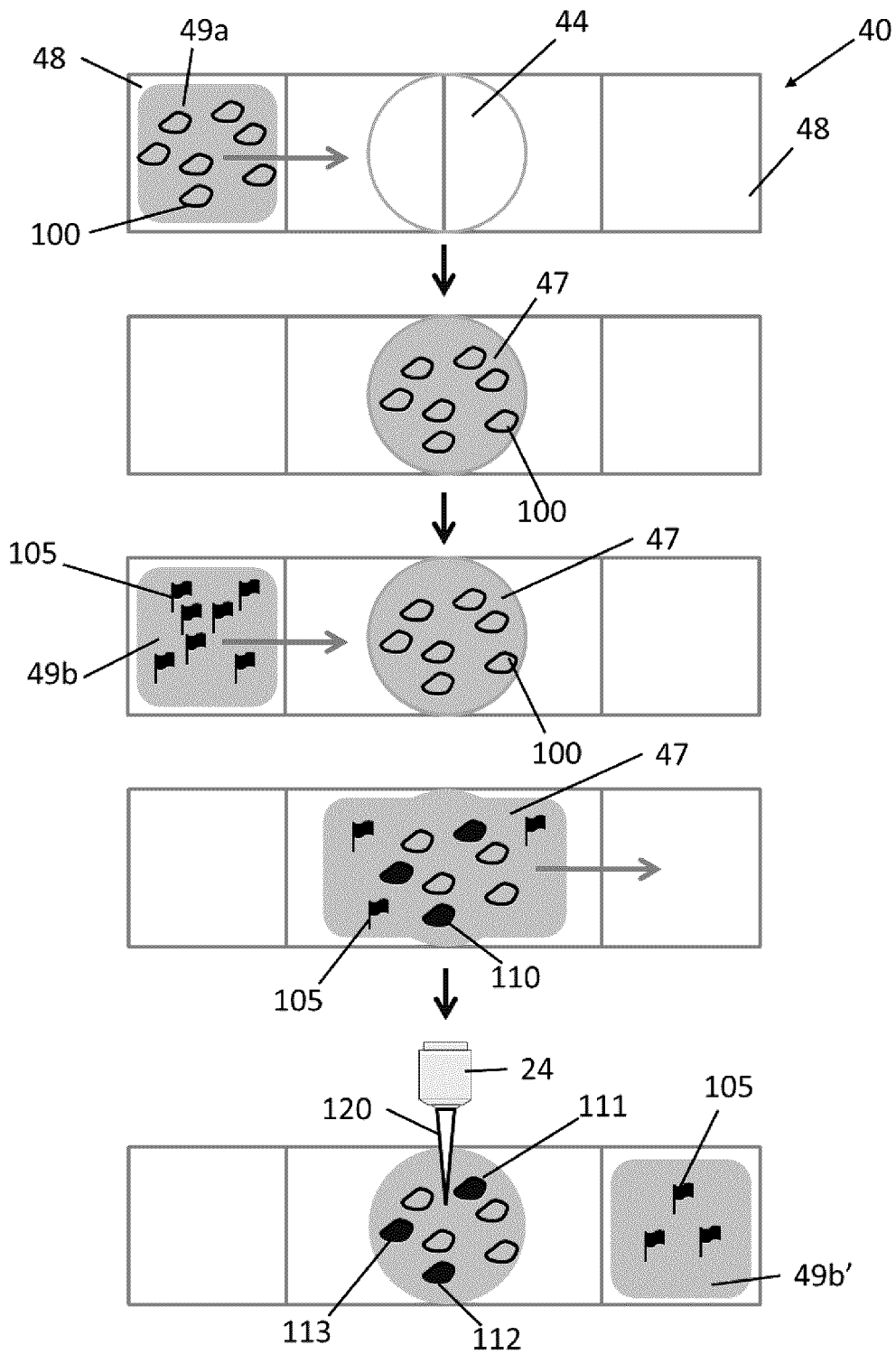
FIGS. 3A and 3B are schematics depicting the use of a system for identifying and targeting individual cells within a cell population for selective extraction of cellular content according to an embodiment of the present disclosure.

According to an embodiment, as shown in FIG. 3A, a sample containing heterogeneous cells 100 may be introduced on the DMF device 40. The sample may be introduced into reservoir 48 under the form of a droplet 49a. The droplet 49a containing the cells 100 is then displaced on the DMF device 40 from the reservoir 48 towards to the hydrophilic site 44 through active dispensing. Once the cells 100 have reached the hydrophilic site 44, the virtual microwell 47 is formed by passive dispensing and the cells 100 may be cultured for a sufficient amount of time to achieve cellular adhesion on the hydrophilic site 44. Alternatively, prior assembly of the DMF device 40 by assembling the top plate 42 onto the bottom plate 41, the sampled cells 100 may be introduced onto the hydrophilic site 44 of the top plate 42, and optionally cultured, and the DMF device 40 is then assembled and mounted onto the motorized stage 32. In this embodiment, the sampled cells 100 may be a cell suspension introduced as a droplet, part of a biopsied tissue sample or a smear (e.g. cells are contained within a sample having high extracellular matrix content, highly viscous in nature) onto the hydrophilic site 44.

As shown in FIG. 3A, cells 100 present within the virtual microwell 47 are then labelled with imaging reagents that interact with or bind to cell-specific markers, surface and/or intracellular, to identify targeted cells 110 using techniques well known in the literature. The imaging reagents may include but are not limited to cell stains such as DAPI and eosin and/or fluorescent dyes such as fluorescein derivatives, BODIPY derivatives, cyanine derivatives, etc. The imaging reagents may include binding agents that bind to cell specific markers, including but are limited to antibodies conjugated to a detectable label such as the fluorescent dyes listed above. Immunofluorescence staining protocols for DMF applications known to be suitable by the skilled person may be used. For example, the protocol described by Ng et al. may be used for immunocytochemical labelling the cells for the purpose of the present invention [15].

It will be appreciated by one skilled in the art that any label that can be detected by physical, chemical, spectroscopic, photochemical, biochemical, immunochemical, electrical, optical, electromagnetic and other related analytical methods may be conjugated to an imaging reagent, in particular a binding agent. A detectable label that may be utilized includes, without limitation, a radioisotope, fluorophore, chromophore, mass label, electron dense particle, magnetic particle, spin label, chemi-luminescent molecule, electro-chemically active molecule, enzyme, cofactor, and enzyme substrates. In aspects of the disclosure, the label is a binding agent disclosed herein or known in the art. In aspects of the disclosure, the label is an immunocytochemical label, in particular an antibody.

The immunocytochemical labelling reagents or stains and dyes or similar imaging reagents 105 may be introduced into reservoir 48 under the form of a droplet 44b. The droplet 44b containing the reagents 105 may be then displaced on the DMF device 40 from the reservoir 48 towards the virtual microwell 47 through active dispensing. The droplet 44b may then be actuated through the virtual microwell 47 for immunocytochemical labelling. Once the labelling has been done, the fluid containing the excess of immunocytochemical labelling reagents 105 is carried to the opposite reservoir 48 as droplet 49b'. According to an embodiment, the step of immunocytochemical labelling the cells may comprise additional steps such as introduction of additional reagents, washes, etc.

According to an embodiment, the step of immunocytochemical labelling the cells 100 may comprise the step of fixing the cells prior to labelling. The fixing step may comprise the use of any acceptable fixative agent known in the art. The fixing step may comprise the use of denaturing fixative or crosslinking fixative. Non-limiting examples include paraformaldehyde, methanol, ethanol, acetone, and glutaraldehyde. The system 1 may perform the lysis of cells that are fixed or live. Live cells have limited means for selection (e.g., external cell markers and morphology) but may be compatible with a broad range of analysis, such as genomic, proteomic and metabolomics profiling. Fixed cells are more amenable for selection (intracellular markers can be probed by immunocytochemistry) and may be stable over long time periods; however, the analytical techniques amenable for probing their contents may be limited.

Figure 7:
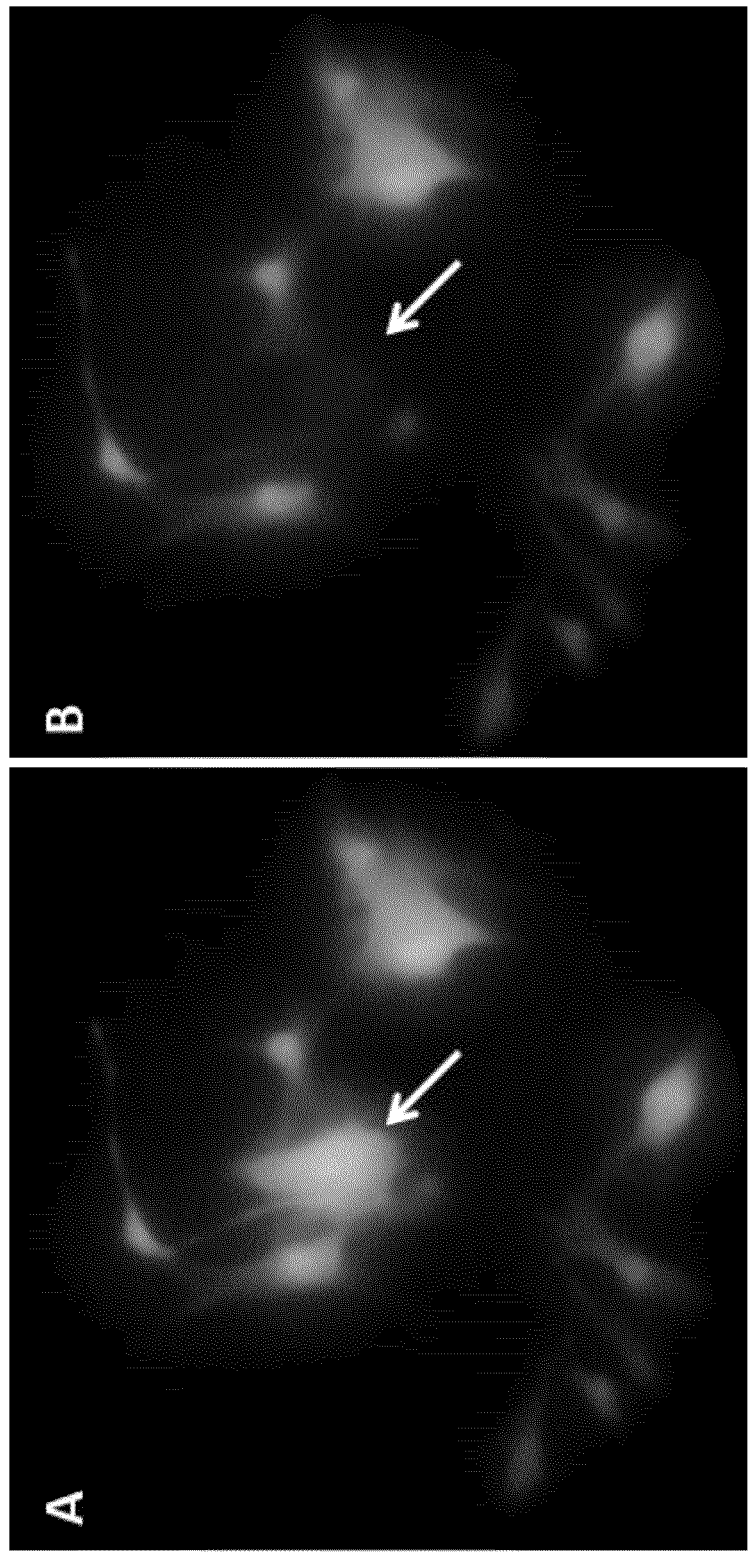
FIG. 7 shows immunofluorescent images of GFP-expressing U87 cells A) before laser microbeam lysis and B) after laser microbeam lysis according to an embodiment of the present disclosure.

According to an embodiment, an adherent cancer cell line, U87, was stably transduced with green fluorescent protein (GFP) and then cultured on a DMF device for two days. As shown in FIGS. 7A and 7B, a particular cell was targeted with a 3-nanosecond laser pulse and its lysate content was collected immediately after lysis, showing that the cell has been lysed and is no longer visible.

Figure 6:
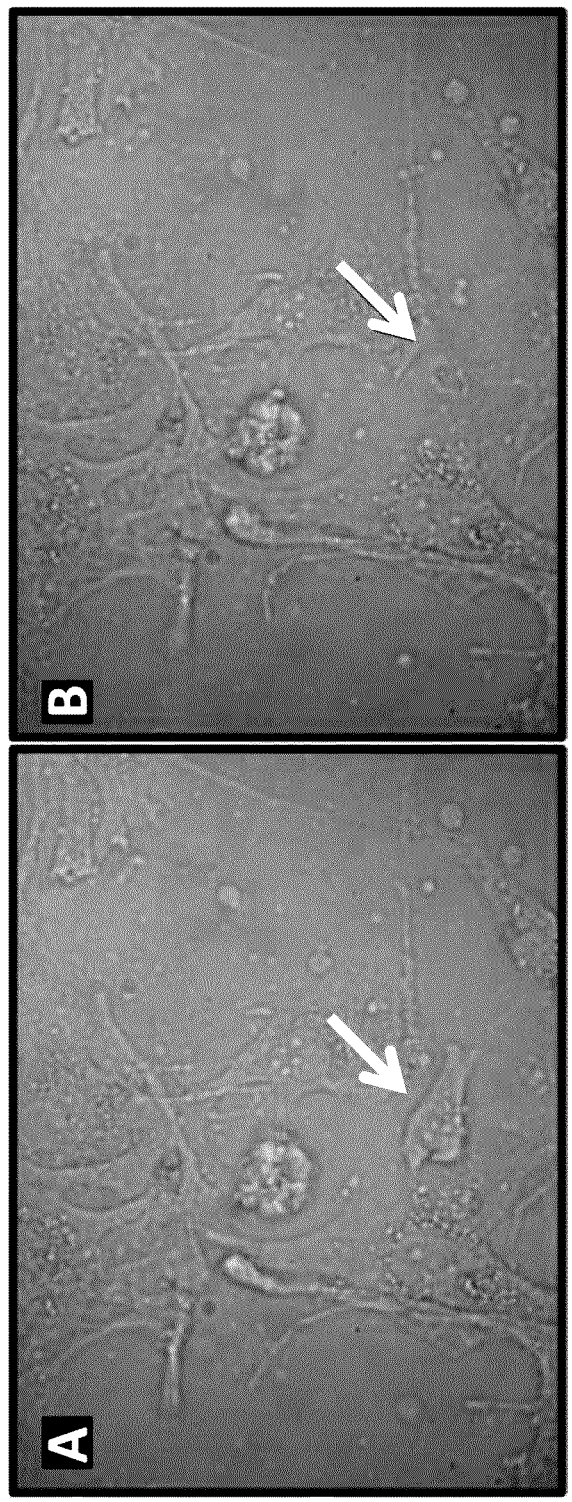
FIG. 6 shows brightfield images of trophoblast cells A) before laser microbeam lysis and B) after laser microbeam lysis according to an embodiment of the present disclosure.

FIGS. 6A, 6B and 7A, 7B exemplify the flexibility of the system 1 to lyse both fixed and live cells on DMF devices. According to an embodiment, FIGS. 6A and 6B display lysis of paraformaldehyde-fixed trophoblast cells from the CVS isolation (6A prior to lysis and 6B after lysis). For the laser lysis, the media was replaced with PBS and cells were lysed into the PBS droplet as shown in FIGS. 6A and 6B. The lysate was then used for genotyping.

Figure 8:
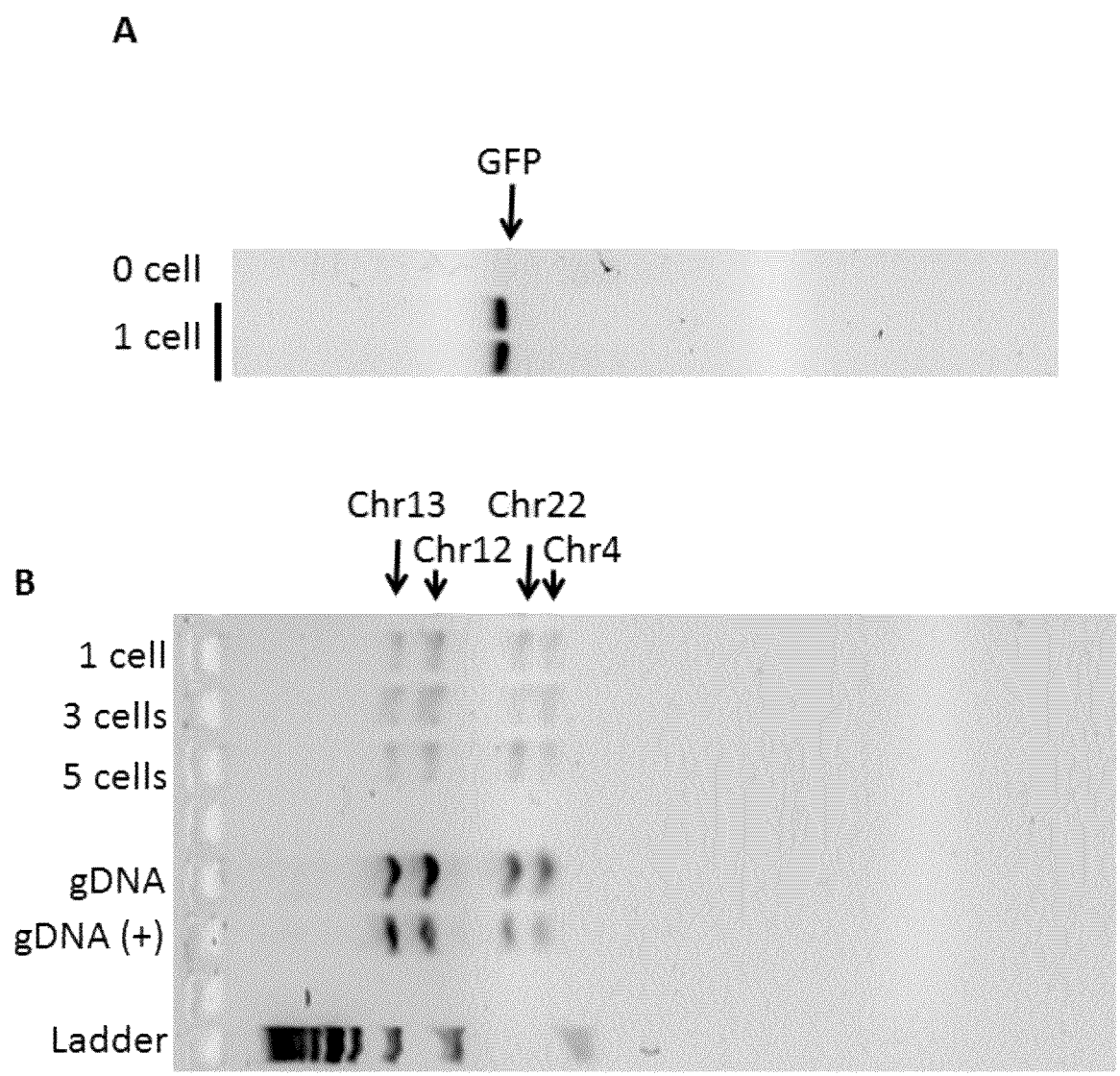
FIG. 8 shows PCR analysis of a single laser lysed cell. A) The detection of the GFP gene by whole genome amplification and PCR from the lysis of single GFP-expressing U87 cells. B) The detection of short tandem repeats of four chromosomes from 1, 3 or 5 laser lysed cells.
Figure 9:
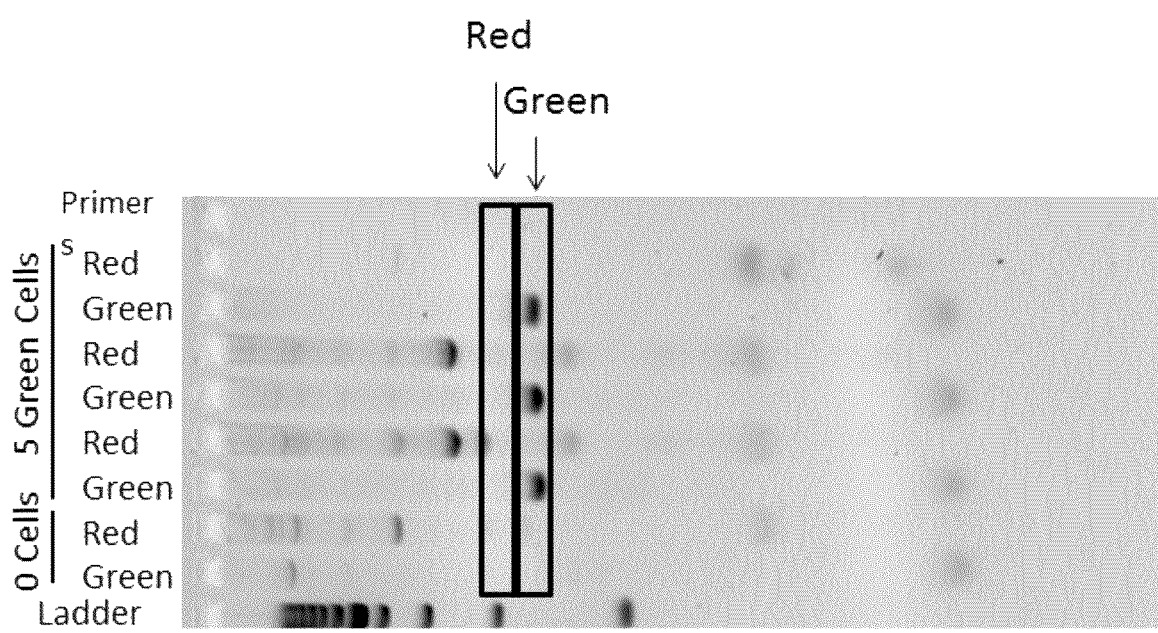
FIG. 9 shows that only the specifically targeted cells are lysed. Red (B16-tdTomato) and green (U87-GFP) cells where mixed together and 5 green (GFP) cells where lysed. PCR was then used to detect the presence of either the GFP or the tdTomato gene in the cell lysate. Only the GFP gene was detected in the lysate indicating that the red cells surrounding the green cells where not lysed.

According to another embodiment, FIGS. 7A and 7B display lysis of live cells, using the U87 cell line (7A prior to lysis and 7B after lysis). U87 cells stably transduced with green fluorescent protein (GFP) were cultured on a DMF device for two days. As shown in FIGS. 7A and 7B, a particular cell was targeted with a 3-nanosecond laser pulse and its lysate content was collected immediately after lysis, showing that the cell has been lysed and is no longer visible. The cell lysate generated from a single U87 cell was collected and the whole genome was amplified by MDA and the resulting sample was analyzed by PCR for the GFP gene to show that it is possible to obtain results from a single cell as shown in FIG. 8A. FIG. 8B shows the PCR analysis for short tandem repeats on four chromosomes indicating that there is a high level of genome coverage generated from the laser lysis of cells. As shown in FIG. 9, only the cells targeted for lysis are lysed. Red (B16-tdTomato) and green (U87-GFP) cells where mixed together and 5 green (GFP) cells where lysed via the laser microbeam. Whole genome amplification and PCR were then used to detect the presence of either the GFP or the tdTomato gene in the cell lysate. Only the GFP gene was detected in the lysate indicating that the red cells surrounding the green cells where not lysed.

Once the cells 100 have been immunocytochemically labelled, the imaging system 30 may use the imaging module 20 to generate images of the virtual microwell 47 in brightfield imaging for size and shape discrimination and fluorescence imaging for detection of the nucleus and labelled cells 110 tagged with the cell-specific biomarkers. FIGS. 6A and 6B show the lysis of trophoblast cells in brightfield imaging and FIGS. 7A and 7B show the lysis of U87 cells in fluorescence imaging respectively. Image analysis software, such as CellProfiler™ (http://cellprofiler.org/), may be used to determine the cells of interest based on the labeling pattern of the cell markers and cell size/shape. The captured images may be processed by machine learning algorithms to identify the targeted cells 110 and plot their locations in the virtual microwell 47 to generate a map of the locations of the targeted cells 110. Algorithms relying on biomarkers and cell size/shape may be implemented to identify the targeted cells to be lysed, e.g., cells 111, 112 and 113 (FIG. 3A).

Furthermore, the cells may be targeted based on cell morphology and phenotype, including but not limited to cell size, shape, surface marker, intracellular marker, dye/drug uptake, etc.

According to an embodiment, the cells may be targeted based on positive and/or negative selection.

Figure 4A:
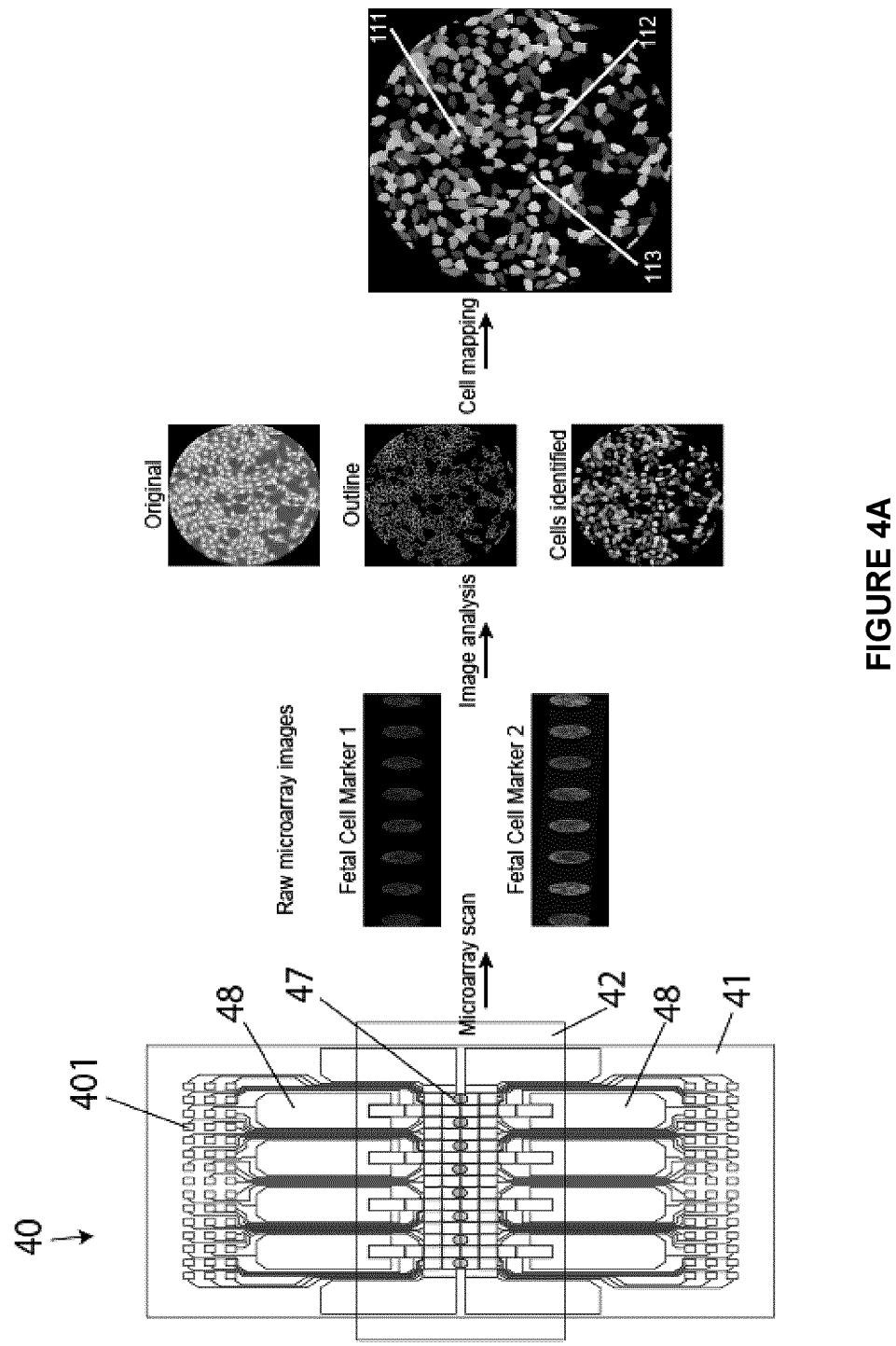
FIG. 4A shows a schematic depicting a cell mapping step according to an embodiment of the present disclosure.

FIG. 4A illustrates an example of the mapping process where cultured cells are labelled with biomarkers such as Fetal Cell Marker 1 and Fetal Cell Marker 2. The cells are then imaged and image analysis and cell mapping are performed to identify and select targeted cells, such as cells 111, 112 and 113. During the cell mapping, algorithms may be applied to determine an optimal displacement path for the motorized stage 32 between cells 111, 112 and 113.

Once the mapping has been performed and the targeted cells have been selected, the system 1 may adjust its operation mode from imaging mode to cell lysis mode. The targeting map is then used to move the DMF device 40 so that a selected targeted cell, such as cell 111, 112 or 113, is brought into the laser microbeam 120 path for lysis. After the selected targeted cell is lysed, one or more droplets 49 may be passed over the virtual microwell 47 to collect the cellular contents and the automated targeting system moves the DMF device to the next cell.

Figure 4B:
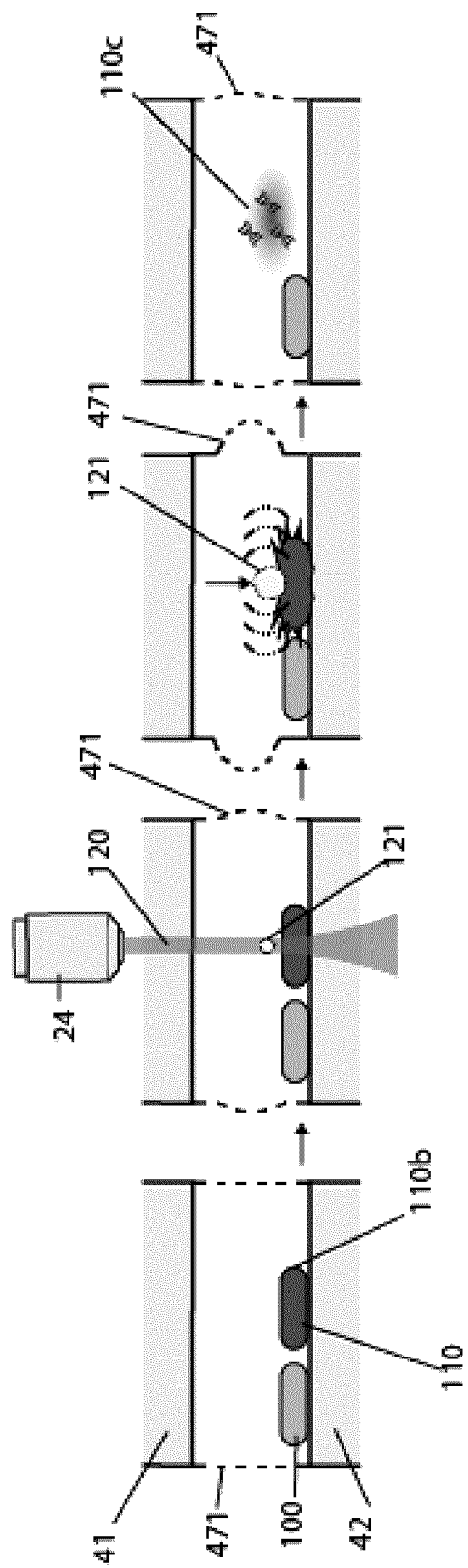
FIG. 4B shows a schematic depicting a laser microbeam lysis of a selected cell according to an embodiment of the present disclosure.

Now referring to FIG. 4B, once the adhered cells 100 have been cultured and immunocytochemically labelled, a labelled cell 110 is selected. A high-energy nanosecond-pulsed laser beam 120 may be focused through the front and rear optical lenses of the imaging device 30, producing a microscopic plasma bubble 121 in proximity to the targeted selected cell 110. The plasma bubble 121 expands rapidly and with enough force to disrupt the cell membrane 110b and lyse the selected labelled cell 110 releasing the cell content 110c as cell lysate 114 into the surrounding solution of the virtual microwell 47. According to an embodiment, the pulsed laser source 11 may fire the laser beam 120 for a duration of 3 nanoseconds leading in the formation of the plasma bubble 121 and the collapse of the targeted labelled cell 110.

According to another embodiment, the lysis may be done in a very short period of time such as 0.5 seconds or less per cell. The "wall" of the virtual microwell 47 or virtual vertical wall 471 may be simply defined by the air-liquid interface of the droplet that is held in place at the hydrophilic site 44 by surface tension of the liquid. This means that the virtual vertical wall 471 is flexible and deformable which allows the absorption of the energy of the expanding plasma bubble by expanding/deforming as the bubble grows and then snapping back into the original shape afterwards based on the lowest energy state of the air/liquid interface without damaging the DMF device 40.

Alternatively, the plasma bubble 121 may lyse the selected labelled cell 110 and other cells that are within a few micrometers (μm) of the focal spot releasing the contents of a plurality of cells as cell lysate into the surrounding solution of the virtual microwell 47.

In one particular embodiment, the technique may be carried out using substrates formed from optically transparent materials (e.g., glass microscope slides similar to those used to form DMF devices) for sampling of adherent cell contents by capillary electrophoresis [16-18] as shown in U.S. Pat. No. 6,156,576, which is incorporated herein by reference in its entirety.

According to an embodiment, the repetition rate (or pulse repetition frequency) and the pulse energy of the pulsed laser source 11 may be adjusted according to the type of cells, state of the cells and the material of interest to be collected. According to an embodiment, one or more laser pulses may be needed to lyse the cell 110.

As the laser microbeam lysis process is dependent on achieving very high optical power in a confined volume, if the focal point of the objective 24 is not correctly positioned at the same distance as the targeted cell 110, the defocused portion of the laser beam 120 may not attain high enough power to cause cell lysis. For this reason, it is preferable (but not essential) to maintain correct focus for the lysis of each selected labelled cell 110. As factors such as changes in temperature and deviations from planarity of the DMF top plate 42 may influence the focal point of the objective 24 or the distance between the selected labelled cell 110 and the objective 24, the focus must be adjusted for each selected cell 110 using an autofocus system.

According to an embodiment, the autofocus system (not shown) may use a simple software feature that adjusts the vertical position of the motorized so stage 32 to maximize the contrast detected by the coupled imaging module 20. Alternatively the autofocus system may comprise an active sensor to measure the distance between the objective 24 and the inner surface of the DMF top plate 42 improving the speed of focusing. In addition, slight changes to the lysis module 10 conveying the laser microbeam 120 to the objective 24, for instance due to temperature or vibration, may change the angle at which the laser beam 120 enters the objective 24, altering the focal point of the laser microbeam 120. Because the plasma bubble 121 produced affects only a small area, a small change in the point of impact may impair proper cell lysis. To prevent this, the focal point of the laser beam 120 may be measured by placing a test substrate with a fluorescent coating on the motorized stage and low power laser pulses applied to image the actual focal point. With this information updated as needed, the placement of the stage 32 may be corrected by the control system 3 to position the laser focal point in the intended location.

To efficiently lyse a multitude of cells in sequence, it may be desirable to minimize the distance the motorized stage 32 has be moved to reach all the cells, reducing the time required per sample. Using the data acquired during the mapping process, algorithms may be applied to determine an optimal displacement path for the motorized stage 32 to move from one to another selected targeted cell 110.

Figure 3B:
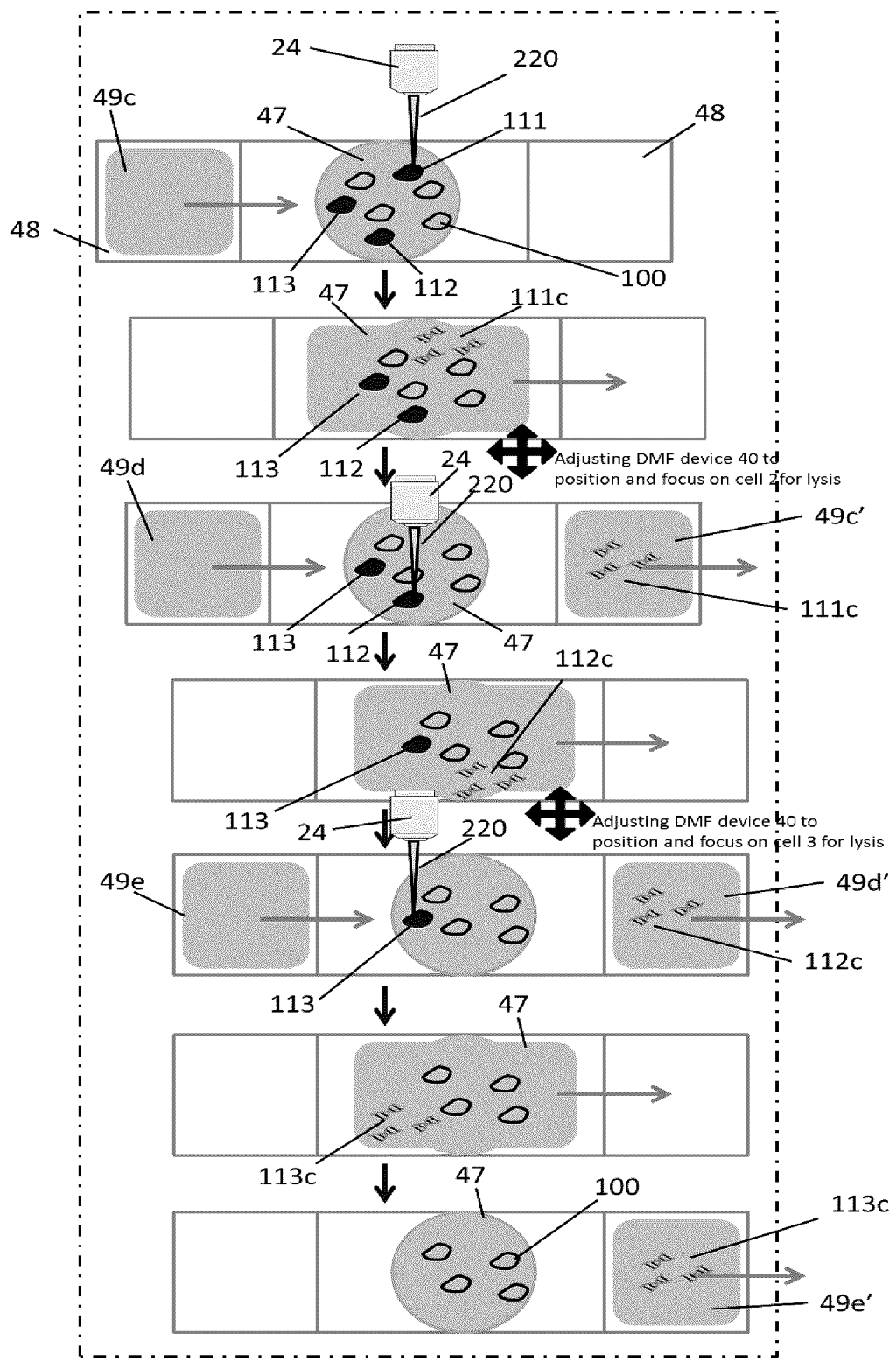
Figure 5:
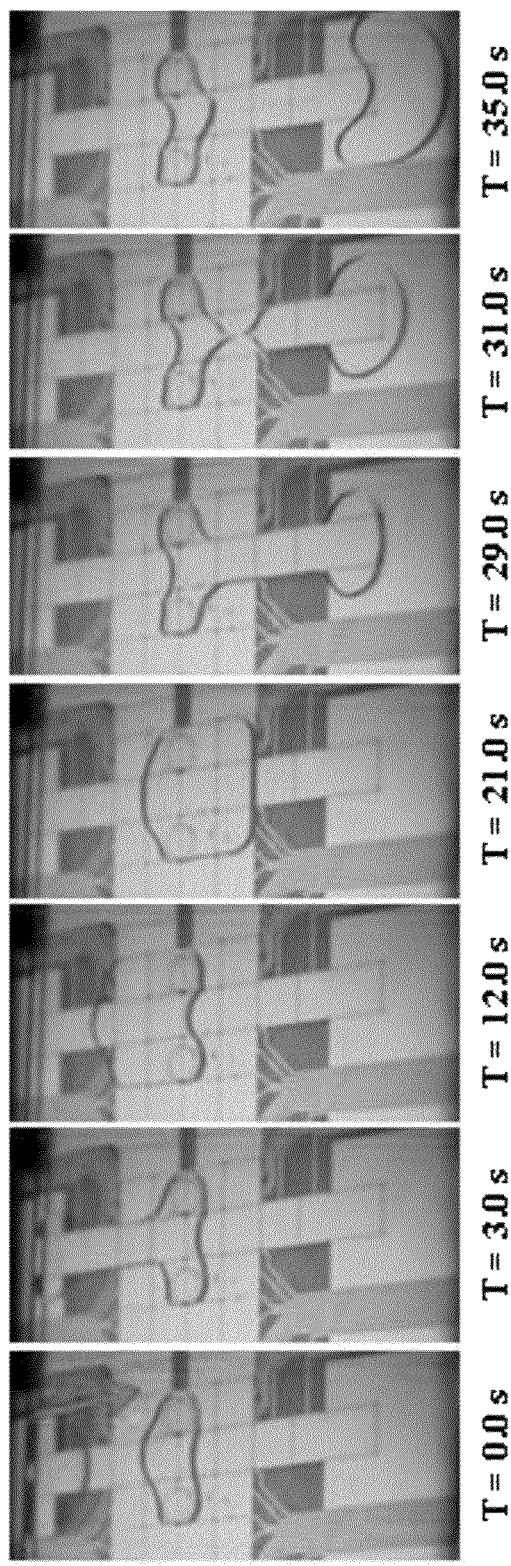
FIG. 5 shows captured images of passive dispensing of a droplet for the removal of cell lysis lysate from the virtual microwell according to an embodiment of the present disclosure.

As shown in FIG. 3B, after cells 100 were cultured on the hydrophilic site 44, a selected cell or plurality of selected cells from the labelled cells 110 is lysed by laser microbeam lysis. As shown in FIG. 3B and FIG. 5, once the selected labelled cell or cells 110 is/are lysed within the virtual microwell 47, the droplet of liquid covering the cells is replaced with a new droplet. A fresh droplet 49 of reagent may be dispensed from the reservoir 48 and may then be driven through the virtual microwell 47, displacing the original fluid droplet 49 that contains the cell lysate. The original fluid is carried to a reservoir 48 on the opposite side of the device 40.

As shown in the still images of FIG. 5, a fresh droplet 49 is dispensed from the reservoir 48 on one side of the device 40 as shown and then driven through the virtual microwell 47, displacing the original fluid in the virtual microwell 47 that contains the cell lysates. The original fluid is carried to a reservoir 48 on the other side of the device 40. The observation that droplets 49 are moveable before and after lysis demonstrates that the laser microbeam plasma bubble 121 does not damage either surface of the DMF device 40 and that droplet 49 movement is unhindered after lysis. This is an indication that the use of lysis module to extract cellular content of a targeted cell cultured within a DMF device may be compatible with DMF technology.

Prior to reaching the reservoir 48 on the other side of the device 40, the droplet 49 containing the cell lysate 112 may be further manipulated on the DMF device 40. Once the droplet 49 reaches the other side reservoir 48, the droplet 49 may be then collected for downstream analysis off-chip or used for on-chip analysis. By carefully controlling the timing of the laser illumination in synchronicity with the droplet movement through the use of the control system 3, one may generate arrays of droplets containing the contents of single cells (or the contents of multiple cells, if desired) within a short period of time. According to an embodiment, the DMF device 40 may have a multitude of reservoirs 48 on both side of the device (as shown in FIG. 2). Once the droplet 49 has collected the cell lysate from the virtual microwell 47, the droplet may be divided and the resulting droplets may be displaced to the same reservoir 48 or displaced to different reservoirs 48.

According to an embodiment, when successively lysing a multitude of cells 110, such as cells 111, 112 and 113, the droplets 49c', 49d' and 49e' may be carried to the same reservoir 48. Under such set-up, cleaning droplets may be introduced on the device 40 to clean the droplet path and the reservoir 48 before the displacement of droplets 49c', 49d' and 49e' to reservoir 48. Alternatively other cleaning means may be used to prevent contamination. According to another embodiment, when the DMF device 40 has a several of reservoirs 48 on both sides of the device (as shown in FIG. 2), each droplets 49c', 49d' and 49e' may be displaced to a different reservoir 48 therefore minimizing contamination.

According to an embodiment of the present disclosure, an advantage of combining the lysis module 10 with the DMF device 40 is the precise control of the illumination timing of the laser microbeam 120 from the pulsed laser source 11, performed by the control system 3 in coordination with the displacement of droplets 49 over the adherent cells 100, performed by the control system 3.

Such coordinated control over the laser microbeam-illumination timing and the droplet displacement enables the user to rapidly generate an array of droplets, each of which may contain the content of an individual cell while minimizing contamination and degradation. Alternatively the contents of multiple cells may be contained within a droplet.

In an embodiment, the DMF device 40, and the imaging system 30 comprising the lysis module 10 and the imaging module 20 may all be controlled (or at least coordinated) by the control system 3 programmed with control software, where steps that do not interfere can be run concurrently (e.g., droplets can move while the stage is repositioning), but checkpoints where certain conditions should be met to proceed will ensure the system is in the correct state at critical points. e.g. the laser source 11 will not fire until the stage 32, DMF device 40 and droplet 49 are in position. Also, the droplet 49 will not be moved away until lysis is confirmed by comparing the camera images before and after;

etc. Automatic error handling could also be performed: droplet movement or laser lysis could be retried if it is detected that the system is not in the correct state, only notifying the operator if the error cannot be corrected.

According to an embodiment, FIG. 3B illustrates the coordination between droplet movement and laser lysis. The droplet 49c is displaced from the reservoir 48 toward the virtual microwell 47 as the laser beam 120 lyses the targeted cell 111 releasing the cell content of cell 111c. Droplet 49c is then driven through the virtual microwell 47 displacing the original fluid in the virtual microwell 47 that contains the cell lysate 111c. The original fluid is carried to the opposite reservoir 48 as droplet 49c'. As droplet 49c' reaches the reservoir 48 and is collected for analysis, a second droplet 49d is displaced from the reservoir 48 toward the virtual microwell 47 as the laser beam 120 lyses the targeted cell 112 releasing the contents of cell 112c.

Droplet 49d is then driven through the virtual microwell 47 displacing the previous fluid in the virtual microwell 47 that contains the cell lysate 112c. The fluid containing the lysate 112c is carried to the opposite reservoir 48 as droplet 49d'. As droplet 49d' reaches the reservoir 48 and is collected for analysis, a second droplet 49e is displaced from the reservoir 48 toward the virtual microwell 47 as the laser beam 120 lyses the targeted cell 113 releasing the contents of cell 113c. Droplet 49e is then driven through the virtual microwell 47 displacing the previous fluid in the virtual microwell 47 that contains the cell lysate 113c. The fluid containing the lysate 113c is carried to the opposite reservoir 48 as droplet 49e'. This process may be repeated until all of the targeted cells 110 are lysed and their contents collected. The lysate for different lysis may be brought to different reservoirs or alternatively collected at the same reservoir.

It will be understood that droplets 49c, 49d and 49e are non-limiting examples and that one or more droplets may be passed through the microwell to collect the lysate content 111c, 112c, and 113c of cells 111, 112, and 113 respectively. As the droplets 49c, 49d and 49e are passed through the virtual microwell 47 under the control of control system 3, the control system 3 displaces the motorized stage 32 to adjust the DMF device 40 to position and focus on the next targeted cell for lysis. To minimize contamination and degradation of the lysate content, the control system 3 in communication with the lysis module 10 timely coordinates the dispensing of the droplets 49, the adjustment of vertical and horizontal positions of the motorized stage 32 and the firing of the pulsed laser source 11.

According to an embodiment, under the control of the control system 3, the lysis-stage displacement-lysis-stage displacement-etc. may be performed on the time scale of about 5 seconds or less per step for movement within a virtual microwell and 15 seconds or less per step when moving between adjacent microwells. Once the lysates 111c, 112c and 113c of selected cells 111, 112 and 113 are collected for off-chip analysis, genomic, metabolomic, transcriptomics and/or proteomic analysis of the lysed cell's contents may be performed and the obtained information may be subsequently correlated to the cell morphology and phenotype information catalogued prior to analysis. These "omic" based analyses are of great importance for many research and clinical applications from the study of stem cells and their differentiation to understand circulating tumour cells and their role in metastatic disease. According to another embodiment, the lysates 111c, 112c and 113c may be collected for on-chip analysis such as ELISA and miRNA detection by electrochemistry or other detection modalities that can interface with DMF devices. The system for identifying and targeting individual cells within a cell population for selective extraction of cellular content 1 may also be configured in a mode to lyse multiple cells before the lysate is collected.

According to an embodiment, to ensure that targeting maps may be imported from external sources or exported to other instruments and that the motorized stage 32 may be moved to position the DMF device 40 accurately, the coordinate space of the imaging system 30 must be aligned with that of the DMF device 40. Because there are always slight changes in position and rotation of the DMF device 40 during fabrication, two or more alignment marks (not shown) may be added to the DMF top plate 42 to be located by the imaging system 30 and may be used as reference points. To locate the marks, the imaging system 30 scans the areas where the marks should be found and their locations can be detected by one of several methods including finding the autocorrelation maximum with a template image of the alignment mark or methods based on feature recognition [20]. Since the positional relationship within the alignment marks and between the marks and the virtual microwells 47 may be defined by the design of the DMF device 40, assuming the device 40 is coplanar with the motorized stage 32, the translation and rotation needed to convert between the coordinates of the DMF device 40 and coordinates of the imaging system 30 may be calculated from the locations of the marks.

According to an embodiment, the control system 3 may be programmed with modules of instructions that define the operating parameters of the system 1. The modules may be independent of each other and may be assembled in different configurations as required. There are a multitude of modules that may be generated depending on the experiments being performed.

Figure 11:
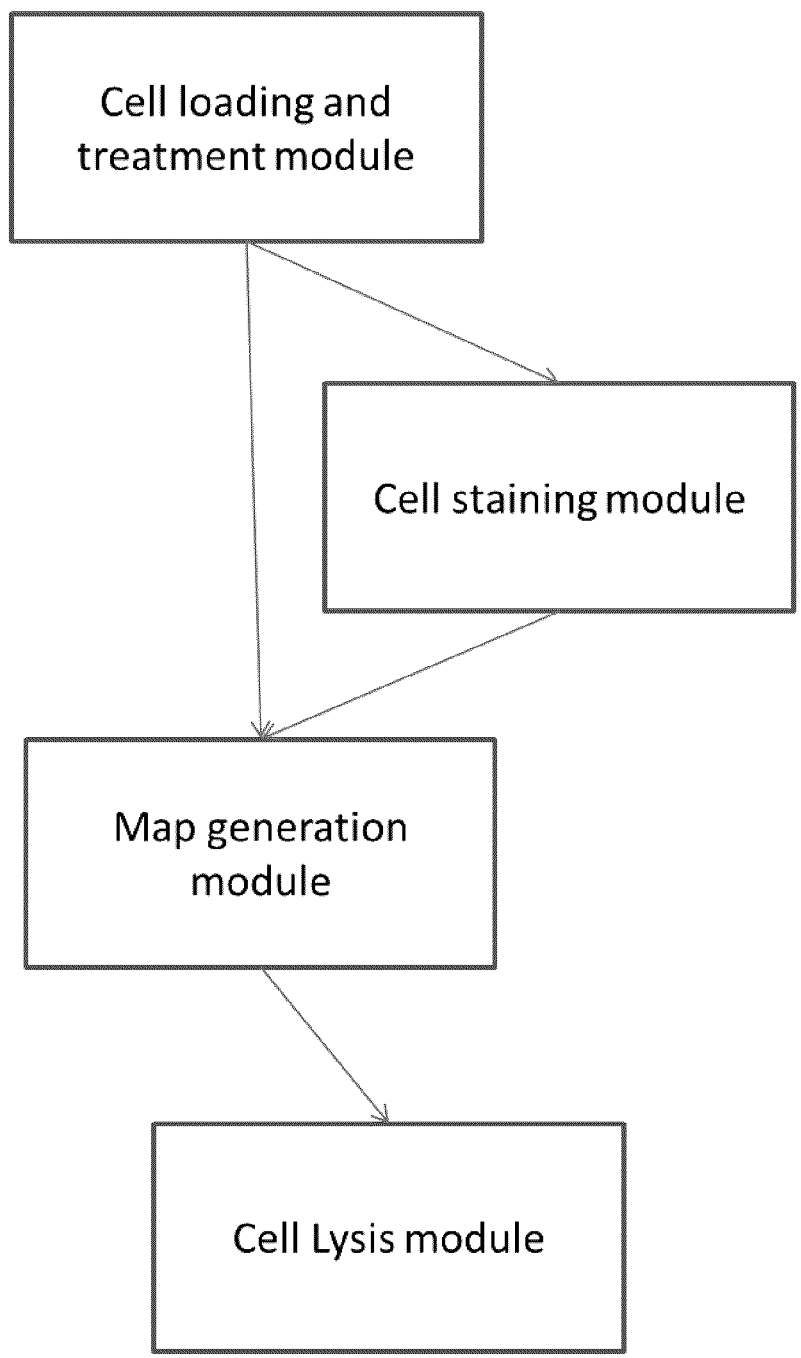
FIG. 11 is a flowchart showing the high level architecture of the interaction of the different modules for automated control cell loading, staining, map generation and cell lysis according to an embodiment of the present disclosure.

According to an embodiment, as shown in FIG. 11, the control system 3 may be programmed with the following modules of instructions fitting together to identify and target individual cells within a population for the selective extraction of cellular content: 1) cell loading and treatment, 2) cell staining, 3) map generation and 4) laser cell lysis.

Figure 12:
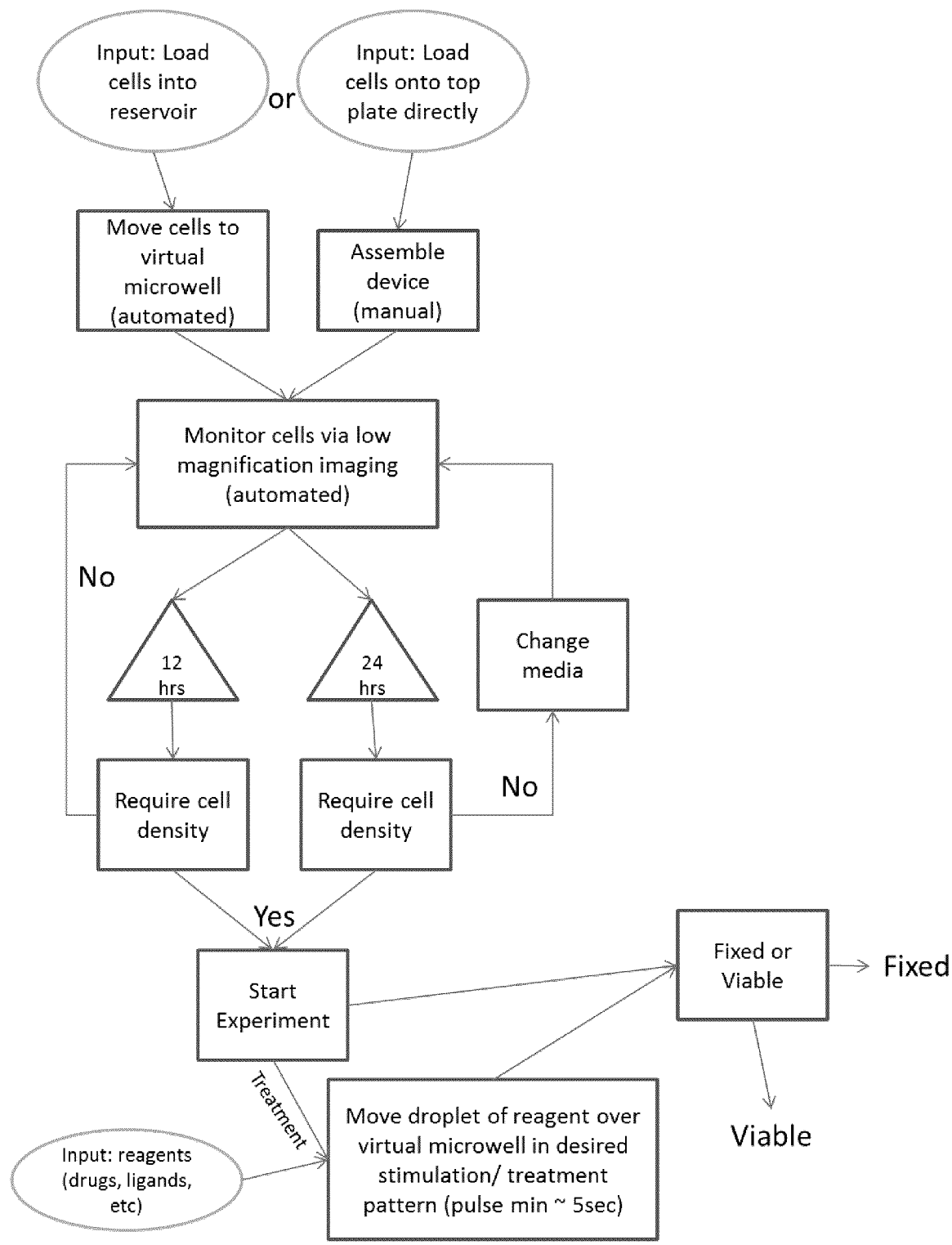
FIG. 12 is a flowchart showing the steps required for automation of cell loading, culture and treatment according to an embodiment of the present disclosure.
Figure 13:
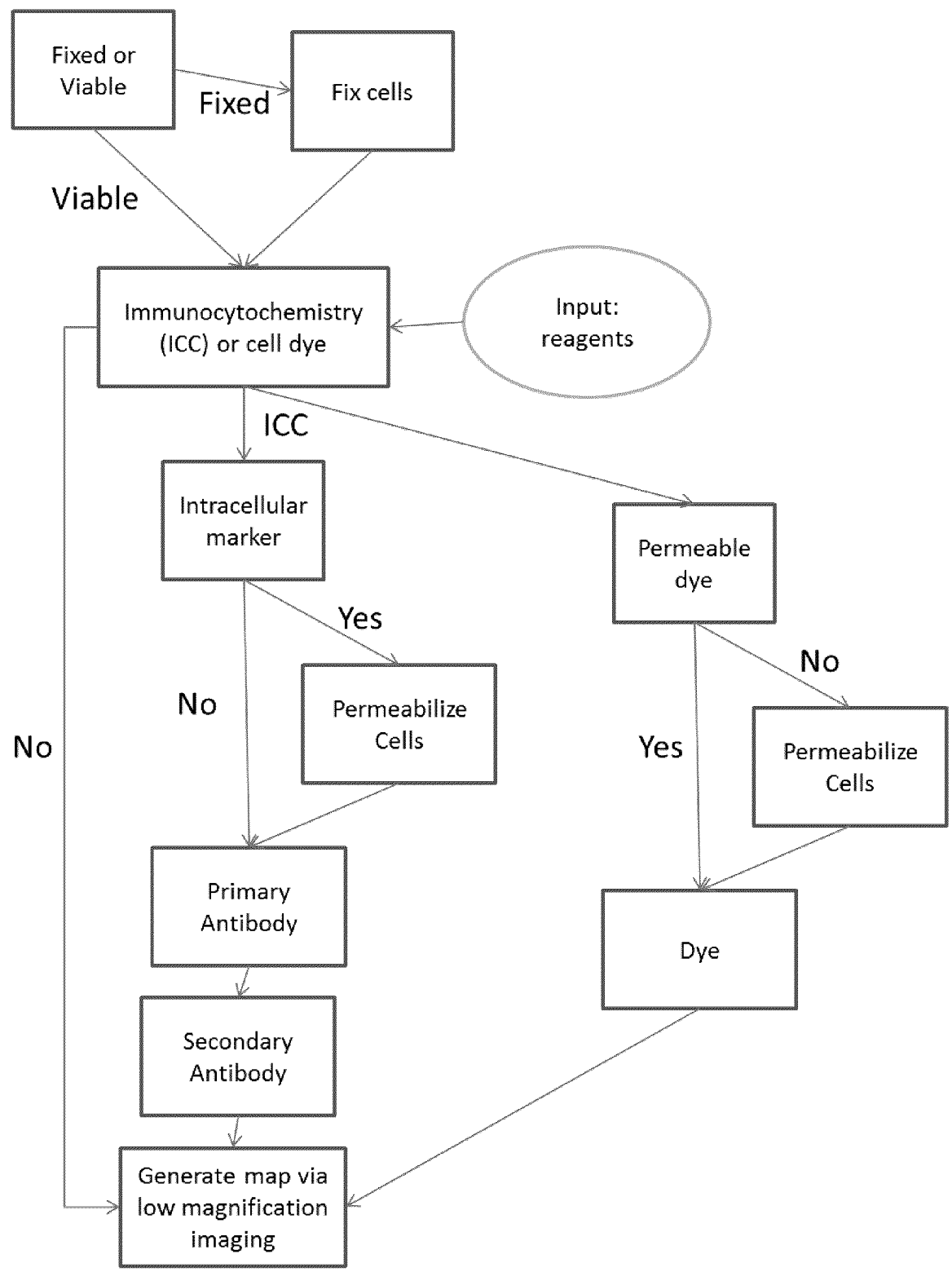
FIG. 13 is a flowchart showing the steps required for automation of cell staining according to an embodiment of the present disclosure.
Figure 14:
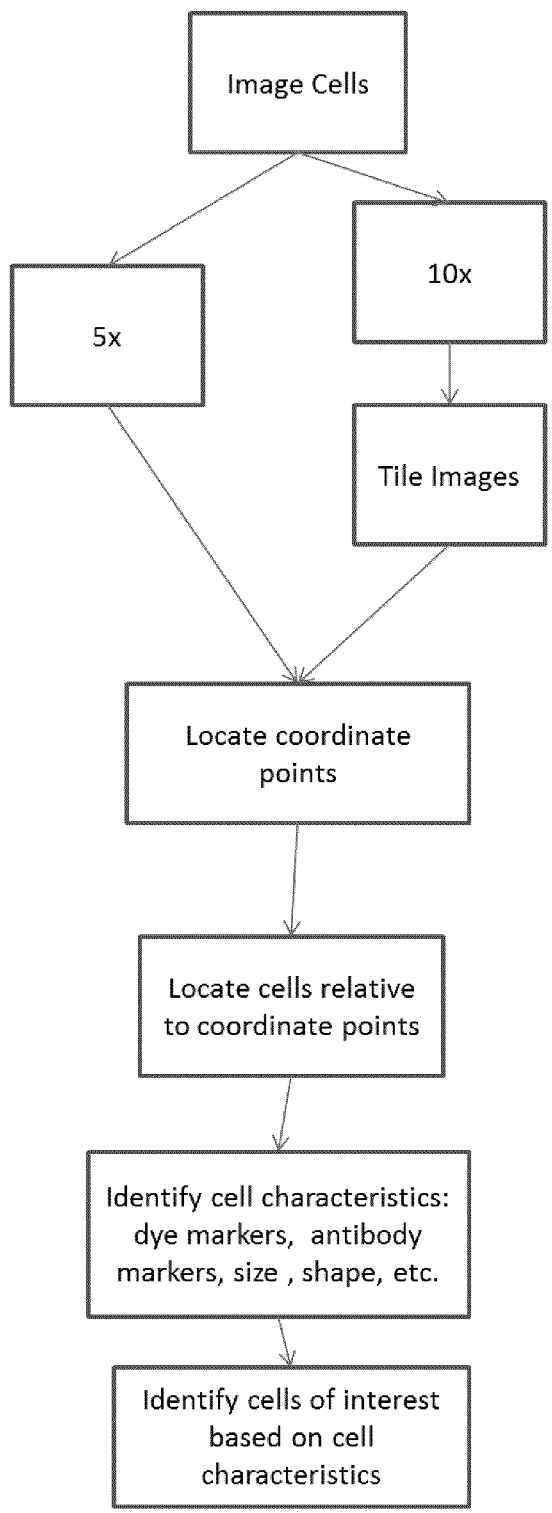
FIG. 14 is a flowchart showing the steps required for automation of cell map generation according to an embodiment of the present disclosure.

An iteration of the automated cell loading and treatment module is shown in FIG. 12. In FIG. 12 and also FIGS. 13, 14 and 15 that are described below, the circles represent inputs to the system (e.g., cells, drugs, etc.). The rectangles are the action and triangles are times. The module, as shown in FIG. 12, may load the cells into the virtual microwells 47 by loading a single cell suspension into the DMF device 40 and the program moving the droplet 49 over the hydrophilic sites 44 to form the virtual microwells 47. If the stage 32 is outfitted with temperature and $CO_2$ controls so that the temperature and $CO_2$ levels of the DMF device 40 are regulated, then the control system 3 may monitor the cell density via the imaging module 20. For live cell imaging and analysis 37° C. and 5% $CO_2$ are the optimal conditions of operation. Note that for fixed cells room temperature and no $CO_2$ can be used for imaging and analysis. Once the desired cell density is reached the control system 3 will automatically treat the cells with different reagent (drugs, ligands, etc.) in various patterns (changes in concentration, duration, etc.).

An example of a possible cell treatment is stimulation with PDGF as demonstrated in Ng et al. (ref. 15). An iteration of the cell staining module (FIG. 13) shows the automated steps required for performing immunocytochemistry on the DMF device 40 and/or treating the cells 100 with a dye or stain (e.g., DAPI). An iteration of the map generation module (FIG. 14) describes the steps require for the control system 3 to identify cells of interest and generate a map of their positions. To generate the map, images of the cells 100 are taken at the lowest resolution required to identify the parameters of interest. For example, if cell size and shape are the parameters then 5× or 10× magnification would be used. However, if the parameters were in subcellular localization of a protein then higher magnification would be required. The images are tiled together to map the entire virtual micro well 47 and this may be used to locate the cells of interest 110. The parameters used to identify the cells of interest 110 may be determined beforehand and inputted into the program. In its simplest form, the parameter may be a cut-off threshold based on cell size. Alternatively the parameter may be a multi-parameter threshold based on several factors. One possible example of this may be machine learning where a training set may be used to develop rules for identification of the cells of interest.

Figure 15:
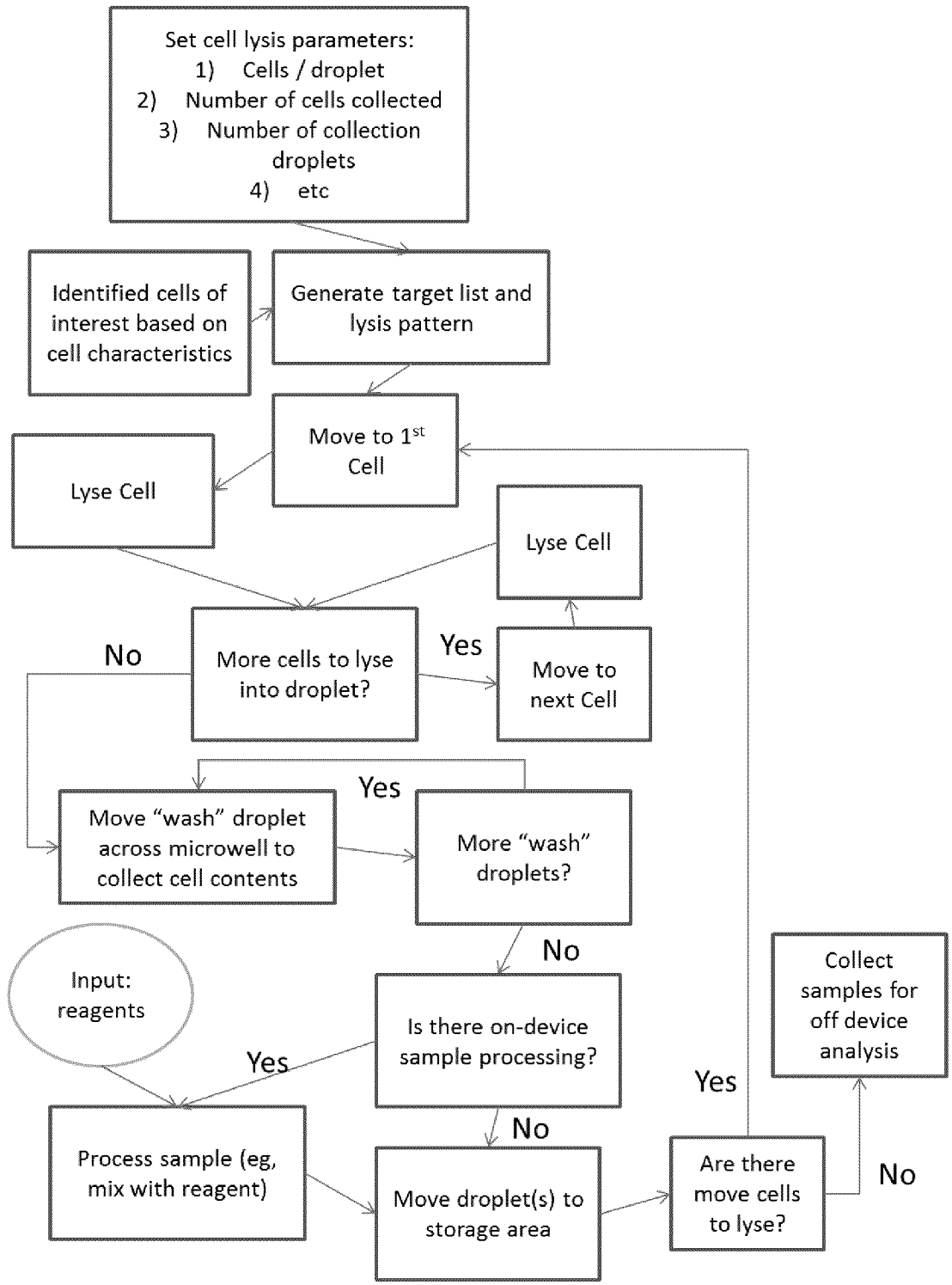
FIG. 15 is a flowchart showing the steps required for automation of cell lysis according to an embodiment of the present disclosure.

FIG. 15 shows an iteration of the cell lysis module which controls the steps of the laser lysis. After the cells of interest 110 are identified, the user may have the options to tell the control system 3 which cells 110 are to be collected (all or a subset of the cells of interest and/or control cells), the number of cells lysed per droplet, etc. From there, the control system 3 may generate a target list and cell lysis pattern (or route). This lysis pattern may minimize the distance traveled between lysis events to minimize the operational time required to lyse all of the targeted cells 110 [21, 22]. If there is any simple on-device sample processing and analysis, this may also be performed automatically by the program and then the droplet 49 may be stored for collect off the device for further analysis. Complex on-device sample processing or analysis may have their own program modules that would run after the cell lysis module. These example modules show the major high level steps and decision points of the workflow therefore some steps may not be shown and each box of the flowchart may have several substeps that are not shown.

According to an embodiment, the systems, methods and kits of the present invention may be used for identification, isolation and/or characterisation of cellular material/analytes as non-invasive testing. In an aspect, the systems, methods and kits may be used as non-invasive diagnostics or screenings for pathological conditions. In another aspect, the systems, methods and kits may be used for non-invasive genetic, genomic, metabolic, transcriptomics and/or proteomic diagnostics and/or screenings. In an aspect, the analytes may include without limitation, nucleic acids, proteins (for example, amino acids, peptides, enzymes, antigens, antibodies, cytokines, lipoproteins, glycoproteins, growth factors or hormones), lipids, carbohydrates, metabolites or combinations thereof. Examples of pathological conditions which may be detected, diagnosed or screened using the systems, methods and kits of the disclosure, include without limitation a cell proliferation condition. Examples of cell proliferation conditions include without limitation, cancers of the colorectum, breast, lung, liver, pancreas, lymph node, colon, prostate, brain, head and neck, skin, liver, kidney, and heart; inflammatory conditions, such as inflammation conditions of the skin; conditions related to obesity; such as proliferation of adipocytes; viral conditions, and cardiac conditions.

In an aspect, the analysis of analytes (e.g., detection and/or levels of proteins and/or characterization) may be determined using a variety of methods known to a person skilled in the art such as immunoassays in various formats such as radioimmunoassay (RIA), chemiluminescence- and fluorescence-immunoassays, enzyme immunoassay (EIA), enzyme-linked immunoassays (ELISA), luminex-based bead arrays, protein microarray assays, and rapid test formats such as immunochromatographic strip tests, and Selected/Multiple reaction monitoring (SRM/MRM). The immunoassay may be a homogenous or heterogeneous assay, competitive or non-competitive. Examples of other methods for analysis of proteins include spectrometry, mass spectrometry, Matrix Assisted Laser Desorption/Ionization Time-of-Flight (MALDI-TOF) Mass Spectrometry, microscopy, northern blot, isoelectric focusing, SDS-PAGE, PCR, quantitative RT-PCR, gel electrophoresis, DNA microarray, protein sequencing, proteome analysis, and antibody microarray, or combinations thereof.

In an aspect, the cellular analyte is nucleic acid. The nucleic acid may be DNA (for example, genomic, mitochondrial, and complementary cDNA from RNA), or RNA (for example, rRNA, mRNA and miRNA). In an aspect, the nucleic acids are nucleotides, oligonucleotides, DNAs, RNAs, or DNA-RNA hybrids. In an embodiment, the nucleic acids are DNAs, in particular, double-stranded DNAs, single-stranded DNAs, multi-stranded DNAs, complementary DNAs, genomic DNAs or non-coding DNAs. In an embodiment, the nucleic acids are RNAs, in particular, messenger RNAs (mRNAs), microRNAs (miRNAs), small nucleolar RNAs (snoRNAs), ribosomal RNAs (rRNAs), transfer RNAs (tRNAs), small interfering RNAs (siRNAs), heterogeneous nuclear RNAs (hnRNAs), or small hairpin RNAs (shRNAs).

Below is a general procedure for processing cells using a system or method of the invention:
 Obtaining a cell sample;
 Generating a single cell suspension from sample
 Loading cell suspension into a DMF device
 Moving the cell suspension as a droplet on at least one site of the DMF device to form a virtual microwell at each of the at least one site
 Immobilizing the cells from cell suspension droplet at the desired site
 Selecting at least one immobilized cell
 Lysing at least one selected cell using a pulsed laser source to produce a lysate within its corresponding virtual microwell
 Displacing a droplet of liquid to the corresponding virtual microwell for collecting the lysate
 Moving the droplet containing the lysate from the corresponding virtual microwell to a designated site.

In an aspect, a method is provided for detecting the presence of an abnormality using rare cells and/or analytes in a sample of a mixed cell population comprising loading the sample on a digital microfluidic system of the disclosure to enrich for the rare cells and/or analytes, and determining the presence or absence of the abnormality by analyzing the enriched rare cells and/or analytes.

In aspects, the systems, methods and kits of the disclosure may be used for detecting rare cells that are in a sample at a concentration of less than 1:2, 1:4. 1:5, 1:10, 1:20, 1:50, 1:100, 1:200, 1:300, 1:400, 1:500, 1:1000, 1:1500, 1:2000, 1:5000, 1:10,000, 1:20,000, 1:50,000, 1:100,000, 1:200,000, 1:500,000, 1:1,000,000, 1:2,000,000, 1:5,000,000, 1:10,000,000, 1:20,000,000, 1:50,000,000, 1:100,000,000 of all cells in the sample. In some embodiments, the sample comprises 2, 3, 4, 5, 6, 7, 8, 9, 10, 20, 30, 40, 50, 60, 70, 80, 90 or 100 rare cells.

According to an embodiment, the cell sample may be used directly as obtained from the source or following a pretreatment to modify the character of the sample. The sample can be derived from any biological source, such as tissues, extracts, cell cultures, and physiological fluids, such as, for example, whole blood, plasma and serum, and can be obtained from any animal subject. Animals can be human or a domesticated animal such as a cow, pig, horse, rabbit, dogs, cat, or goat.

According to an embodiment, the systems, methods and kits of the disclosure may be used with a cell sample that has been processed to be enriched with rare cells.

In an embodiment the present disclosure provides a method for identifying and targeting individual cells within a cell population for selective extraction of cellular content. The method includes loading a sample containing cells on at least one site of a digital microfluidic device thereby forming a virtual microwell at each of the at least one site; Immobilizing the cells on the at least one site; selecting at least one immobilized cell; lysing the at least one selected cell using a pulsed laser source to produce lysate within its corresponding virtual microwell; displacing a droplet of liquid to the corresponding virtual microwell for collecting the lysate; and moving the droplet containing the lysate from the corresponding virtual microwell to a designated site.

The meaning of the terms "immobilizing" and "immobilized" is not limited to "inducing cell adhesion" and "adhered/adherent".

In some embodiments the at least one site for receiving cells may be hydrophilic, partially hydrophilic or become hydrophilic after protein fouling/adsorption from the sample.

In an embodiment the method may include a step of generating a map of locations of the immobilized cells, and wherein the step of selecting the at least one immobilized cell includes selecting the at least one cell from the map.

In an embodiment the method may further comprise a step of labelling the immobilized cells, and this may also comprise fixing the cells.

In an embodiment the method may further comprise the steps of:

moving the digital microfluidic device along horizontal axes and a vertical axis for positioning the digital microfluidic device for lysing another at least one selected cell from immobilized cells;

lysing the other at least one selected cell using the pulsed laser source to produce another lysate within its corresponding virtual microwell;

displacing another droplet of liquid to the corresponding virtual microwell for collecting the other lysate; and moving the other droplet containing the other lysate from the corresponding virtual microwell to a designated site.

In an embodiment the method may further comprise a step of introducing the sample containing the cells at an initial site and displacing the sample to the at least one site.

In an embodiment the at least one site is a plurality of sites, and including steps of moving of droplets to said plurality of sites, selecting of a cells to be lysed at each of said plurality of sites, selecting a first site to illuminate the selected cell at that site, moving of the stage to move the digital microfluidic device sequentially to bring each of the sites into a field of view of the pulsed laser source to lyse the selected cell to produce lysate at each site, and collecting the lysate at each site.

In this embodiment where the at least one site is a plurality of sites, the method may include calculating a shortest distance travelled by the stage to bring each of the plurality of sites into the field of view of the pulsed laser source sequentially.

In another embodiment where the at least one site is a plurality of sites, the at least one selected targeted cell is a plurality of selected targeted cells, and the method may further include identifying a sequence of selected targeted cells to be lysed to minimize a time to perform the lysing on all selected targeted cells, and wherein the plurality of selected targeted cells is within one field of view, or a plurality of field of views, or within a plurality of sites.

In an embodiment of the method the pulsed laser source may be a nanosecond-pulsed laser.

In an embodiment of the method the pulsed laser source may be a nanosecond-pulsed laser delivering pulses of at least 1 µJ.

In an embodiment of the method the nanosecond-pulsed laser may be a Nd-based laser.

In an embodiment of the method the nanosecond-pulsed laser may produce a pulsed-laser beam within the visible spectrum.

In an embodiment of the method the pulsed laser source may be a Q-switched laser.

In an embodiment the method may further comprise the step of performing on chip analysis of the lysate at the designated site and in this embodiment the method may further comprise the step of collecting the droplet containing the lysate from the designated site for off-chip analysis.

Prenatal and Neonatal Diagnostics

The system and method of the present invention may be used for a wide range of applications including, but not limited to: identification of rare fetal cells for genomic analysis for non-invasive prenatal genetic diagnostic screening, identification of circulating tumour cells for cancer diagnostics, differentiation between cells that respond (or not) to a drug, cell analysis based on changes of protein localization, evaluation of stem cells at various stages of differentiation and the identification of congenital anomalies. In an aspect, the system and method of the invention are used for non-invasive prenatal genetic diagnosis of chromosome abnormalities and single gene disorders.

In an aspect, a method is provided for detecting the presence of an abnormality using rare cells and/or analytes in a sample of a mixed cell population comprising loading the sample on a digital microfluidic system of the disclosure to enrich for the rare cells and/or analytes, and determining the presence or absence of the abnormality by analyzing the enriched rare cells and/or analytes.

In aspects, the systems, methods and kits of the disclosure may be used for detecting rare cells that are in a sample at a concentration of less than 1:2, 1:4. 1:5, 1:10, 1:20, 1:50, 1:100, 1:200, 1:300, 1:400, 1:500, 1:1000, 1:1500, 1:2000, 1:5000, 1:10,000, 1:20,000, 1:50,000, 1:100,000, 1:200,000, 1:500,000, 1:1,000,000, 1:2,000,000, 1:5,000,000, 1:10,000,000, 1:20,000,000, 1:50,000,000, 1:100,000,000 of all cells in the sample. In some embodiments, the sample comprises 2, 3, 4, 5, 6, 7, 8, 9, 10, 20, 30, 40, 50, 60, 70, 80, 90 or 100 rare cells. In embodiments of the disclosure, the rare cells are fetal cells, in particular fetal cells in a sample of fetal cells and maternal cells.

The systems, methods and kits of the disclosure may be used in the detection of fetal cells or fetal analytes, and in particular they may be used to detect, diagnose or aid in the diagnosis of prenatal or neonatal conditions. In an aspect, the systems, methods and kits of the disclosure are used to diagnose or aid in the prenatal diagnosis of genetic conditions. Analytes include without limitation, nucleic acids, proteins, lipids, carbohydrates, metabolites, or combinations thereof.

Examples of conditions which may be detected or diagnosed using the systems, methods and kits of the disclosure, include without limitation, autosomal dominant conditions such as achondroplasia, osteogenesis imperfecta, Marfan syndrome, polycystic kidney disease, Waardenburg syndrome, and the like, autosomal recessive conditions such as Cockayne syndrome, cystic fibrosis, Tay-Sachs disease, sickle cell anemia, congenital adrenal hyperplasia, alpha- and beta-thalassemia; X-linked disorders such as fragile X syndrome, Duchenne's muscular dystrophy, hemophilia A and B; imprinting disorders such as Angelman syndrome/Prader Willi syndrome and microscopic and submicroscopic chromosome abnormalities, and the like. (See also, for example, Milunsky A, and Milunsky, J M, editors. Genetic Disorders and the Fetus: Diagnosis, Prevention and Treatment, 7th ed. John Wiley & Sons, 2015 relating to prenatal genetic conditions.)

In embodiments of the disclosure, the prenatal condition is a chromosome abnormality. Chromosome abnormalities include, without limitation, a gain or loss of an entire chromosome or a region of a chromosome comprising one or more genes or an abnormal number of a chromosome. Examples of conditions involving chromosome abnormalities include without limitation, Down syndrome and DiGeorge syndrome, trisomy 13, trisomy 18, trisomy 21 (Down Syndrome), monosomy, triploidy, tetraploidy, Klinefelter's Syndrome (XXY), and other sex chromosome aneuploidies or autosomal chromosome abnormalities and combinations thereof.

In an embodiment, the prenatal condition is a single gene disorder.

In an embodiment, the prenatal condition comprises, is chosen from or is selected from the group consisting of DiGeorge syndrome, trisomy 13, trisomy 18, trisomy 21 (Down Syndrome), Klinefelter's Syndrome (XXY), monosomy, triploidy, tetraploidy and other sex chromosome or autosomal chromosome aneuploidies, and combinations thereof.

In an embodiment, the prenatal condition is a trisomy, more particularly, trisomy 21, trisomy 18, trisomy 13 or a combination thereof.

Examples of other conditions which may be detected or diagnosed using the systems, methods and kits of the disclosure, include without limitation a cell proliferation condition. Examples of cell proliferation conditions include without limitation, cancers of the colorectum, breast, lung, liver, pancreas, lymph node, colon, prostate, brain, head and neck, skin, liver, kidney, and heart; inflammatory conditions, such as inflammation conditions of the skin; conditions related to obesity; such as proliferation of adipocytes; viral conditions, and cardiac conditions.

In an aspect, a method is provided for enriching fetal cells and/or fetal analytes in a sample containing a mixed population of cells (e.g. fetal and maternal cells) comprising subjecting the sample to a microfluidic system of the disclosure having elements for separating and isolating the fetal cells and/or analytes.

In an aspect, a method is provided for obtaining and using fetal cells and/or fetal analytes from a sample to perform prenatal diagnosis the method comprising a microfluidic device of the disclosure having elements for separating and isolating the fetal cells and/or analytes from the sample.

Positive and/or negative selection may be used in the methods of the disclosure. In a particular aspect, the method includes a diagnostic device comprising a microfluidic device of the disclosure having elements to separate and isolate fetal cells and/or fetal analytes from a heterogenous sample, wherein the elements comprise binding agents that bind fetal cell-specific markers and/or maternal cell-specific markers, including surface or intracellular markers. In a particular aspect, the method includes a diagnostic device comprising a microfluidic device of the disclosure having elements to separate and isolate fetal cells and/or fetal analytes from a heterogenous sample, wherein the elements comprise binding agents that bind fetal cell-specific markers, including surface or intracellular markers. In a particular aspect, the method includes a diagnostic device comprising a microfluidic device of the disclosure having elements to separate and isolate fetal cells and maternal cells from a heterogenous sample. In an embodiment, the fetal cell-specific markers may comprise, be chosen from, or be selected from the group consisting of Fetal Cell Marker 1, Fetal Cell Marker 2, 5T4, HLA-G, CD227, β subunit of choronic gonadotropin (β-CG), placental lactogen, cytokeratin 7, placental alkaline phosphatase, NDOG1, PSG1, PSG9, MMP14, MCAM, KCNQ4, CLDN6, F3, PEG10, FLT1, CBG,GCM1, GPA, CD45, EGFR, APOB, CD71, CD36, CD34, HbF, FB3-2, H3-3, HAE 9, FB3-2, HBE, APOC3, AMBP, CPB2, ITIH1, APOH, HPX, AHSG, APOB, BPG, carbonic anhydrase (CA), and thymidine kinase. In an embodiment, the maternal cell-specific markers comprise, are chosen from, are selected from, or selected from the group consisting of CD90, CD73, CD44, CD105, and CD29.

Methods of the disclosure may also select fetal cells based on morphological characteristics such as size and shape (see for example, James et al, Human Reproduction 22(8): 2111-2119, 2007; Bulmer et al, Prenatal Diagnosis 23:34-39, 2003; Moser et al, Placenta 32: 197-199, 2011; and Caruso et al, Int J Mol Cell Med. 1(2): 64-74, 2012, for morphological characteristics of fetal cells).

The methods enable non-invasive acquisition of fetal cells and fetal analytes from a pregnant subject which can be used for a variety of purposes, including but not limited to, the identification of fetal cells in cervical samples, determination of fetal cell density to predict high risk pregnancies, genetic analysis of fetal nucleic acids, determination of the fetal karyotype, genetic analysis of fetal DNA from fetal cells, detection of abnormalities in the fetus, detection of possible complications of pregnancy, and determination of biomarkers or growth factors to predict prenatal and postnatal conditions.

A sample can be used directly as obtained from the source or following a pretreatment to modify the character of the sample. The sample can be derived from any biological source, such as tissues, extracts, cell cultures, and physiological fluids, such as, for example, whole blood, plasma and serum, and can be obtained from any animal subject. Animals can be human or a domesticated animal such as a cow, pig, horse, rabbit, dogs, cat, or goat. In an embodiment, a sample can be obtained from an animal suspected of being pregnant, pregnant, or that has been pregnant, to detect the presence of a prenatal condition.

The system, kits and methods of the disclosure are particularly useful for obtaining fetal cells and fetal analytes from an endocervical sample. Endocervical samples or cervical mucosal samples can be obtained using standard non-invasive procedures known to a person skilled in the art, including but not limited to intrauterine lavage, aspiration of cervical mucus, or removal of surface tissue from the cervical or endocervical canal. In an embodiment, a cervical mucosal sample is obtained from the endocervical canal using a cytobrush. An endocervical sample may be obtained with a commercially available kit such as a ThinPrep® kit (Hologic Corporation, Marlborough, Mass.) which comprises a cytological brush and a fixative solution (which may or may not be used). A sample collection can be incorporated as a sample collection device in a kit disclosed herein.

In an embodiment, the endocervical sample is obtained from the subject during the first trimester of pregnancy. In an embodiment, the endocervical sample is obtained from the subject during the early second trimester of pregnancy.

Samples may be collected from subjects repeatedly at different times, for example, over the term of a pregnancy, and can be used to verify results from earlier detections and/or to identify an alteration as a result of, for example, treatment.

In an aspect, the method includes a diagnostic device comprising a microfluidic device of the disclosure having elements to separate and isolate fetal cells or fetal analytes from maternal cells in an endocervical sample, wherein the elements comprise binding agents that bind fetal cell-specific markers and/or maternal markers, including surface or intracellular markers. In an embodiment, the fetal cell-specific markers comprise, may be chosen from, or be selected from the group consisting of Fetal Cell Marker 1, Fetal Cell Marker 2, 5T4, HLA-G, CD227, β subunit of chorionic gonadotropin (β-CG), placental lactogen, cytokeratin 7, placental alkaline phosphatase, NDOG1, PSG1, PSG9, MMP14, MCAM, KCNQ4, CLDN6, F3, PEG10, FLT1, CBG,GCM1, GPA, CD45, EGFR, APOB, CD71, CD36, CD34, HbF, FB3-2, H3-3, HAE 9, FB3-2, HBE, APOC3, AMBP, CPB2, ITIH1, APOH, HPX, AHSG, APOB, BPG, carbonic anhydrase (CA), and thymidine kinase. In an embodiment, the maternal cell-specific markers comprise, are chosen from, are selected from, or selected from the group consisting of CD90, CD73, CD44, CD105, and CD29.

Binding agents that bind fetal cell-specific markers or maternal cell-specific markers include substances such as polypeptides or antibodies that specifically bind to one or more cell-specific marker, or in some cases an intracellular organelle (e.g., ribosomes, endoplasmic reticulum) or cell nucleic acid. A substance "specifically binds" if it reacts at a detectable level with one or more cell-specific marker, and does not react detectably with polypeptides or peptides containing an unrelated or different sequence. Binding properties may be assessed using methods knows in the art such as an ELISA, which may be readily performed by those skilled in the art (see for example, Newton et al, Develop. Dynamics 197: 1-13, 1993). Examples of binding agents include without limitation ribosomes, with or without a peptide component, aptamers, RNA molecules, and polypeptides, and in particular antibodies. Antibodies may be synthetic antibodies, monoclonal antibodies, polyclonal antibodies, recombinant antibodies, antibody fragments (such as Fab, Fab', F(ab')2), dAb (domain antibody; see Ward, et al, 1989, Nature, 341:544-546), antibody heavy chains, intrabodies, humanized antibodies, human antibodies, antibody light chains, single chain $F_{vs}$ (scFv) (e.g., including monospecific, bispecific etc.), anti-idiotypic (ant-Id) antibodies, proteins comprising an antibody portion, chimeric antibodies (for example, antibodies which contain the binding specificity of murine antibodies, but in which the remaining portions are of human origin), derivatives, such as enzyme conjugates or labeled derivatives, diabodies, linear antibodies, disulfide-linked $F_{vs}$ (sdFv), multispecific antibodies (e.g., bispecific antibodies), epitope-binding fragments of any of the above, and any other modified configuration of an immunoglobulin molecule that comprises an antigen recognition site of the required specificity. An antibody includes an antibody of any type (e.g. IgA, IgD, IgE, IgG, IgM and IgY), any class (e.g. IgG1, IgG2, IgG3, IgG4, IgA1 and IgA2), or any subclass (e.g. IgG2a and IgG2b), and the antibody need not be of any particular type, class or subclass. An antibody may be from any animal origin including birds and mammals (e.g. human, murine, donkey, sheep, rabbit, goat, guinea pig, horse, or chicken). A binding agent may be labelled with a detectable label as disclosed herein. A binding agent labelled with a detectable label is sometimes referred to herein as an imaging reagent.

In an aspect the disclosure provides a method for retrieving fetal analytes from a sample, in particular an endocervical sample, comprising (i) obtaining the sample, in particular an endocervical sample; (ii) introducing the sample into a microfluidic system of the disclosure that allows separation and isolation of fetal cells, and (iii) producing from the fetal cells a lysate comprising fetal analytes.

In an aspect, the disclosure provides a method for detecting and/or isolating fetal analytes from a sample, in particular an endocervical sample, comprising a mixed population of cells, in particular fetal cells and maternal cells, the method comprising introducing the sample into a microfluidic system that allows (i) separation and isolation of the fetal cells in the sample, (ii) lysis of the isolated fetal cells, and (iv) detection and/or isolation of fetal analytes from the lysed fetal cells. The microfluidic system may optionally comprise culturing of cells in the sample to enrich for fetal cells. In an embodiment, the system comprises a digital microfluidic device of the disclosure, and elements to separate and isolate fetal cells from other cells in an endocervical sample such elements, chosen from, selected from, or selected from the group consisting of binding agents that bind one, two or more fetal cell-specific markers and/or maternal cell-specific markers. In an embodiment, the fetal-cell specific markers comprise, may be chosen from or be selected from the group consisting of Fetal Cell Marker 1, Fetal Cell Marker 2, 5T4, HLA-G, CD227, β subunit of chorionic gonadotropin (β-CG), placental lactogen, cytokeratin 7, placental alkaline phosphatase, NDOG1, PSG1, PSG9, MMP14, MCAM, KCNQ4, CLDN6, F3, PEG10, FLT1, CBG,GCM1, GPA, CD45, EGFR, APOB, CD71, CD36, CD34, HbF, FB3-2, H3-3, HAE 9, FB3-2, HBE, APOC3, AMBP, CPB2, ITIH1, APOH, HPX, AHSG, APOB, BPG, carbonic anhydrase (CA), and thymidine kinase. In an embodiment, the maternal cell-specific markers comprise, are chosen from, are selected from, or selected from the group consisting of CD90, CD73, CD44, CD105, and CD29. The binding agents may be labelled with a detectable label as disclosed herein.

In an aspect, the fetal analyte is a fetal protein, (for example, amino acids, peptides, enzymes, antigens, antibodies, cytokines, lipoproteins, glycoproteins, growth factors or hormones). In an embodiment, the fetal analyte is a growth factor.

In an aspect, a method is provided for detecting or isolating a fetal protein from a sample comprising fetal cells, the method comprising introducing the sample into a microfluidic system that allows (i) separation and isolation of fetal cells in the sample; (ii) lysis of the isolated fetal cells, (iii) detection or isolation of a fetal protein from the lysed fetal cells, and (iv) optionally analysis of the fetal protein. The microfluidic system may also comprise culturing of cells in the sample to enrich for fetal cells.

The analysis of proteins (e.g., detection and/or levels of proteins) may be determined using a variety of methods known to a person skilled in the art such as immunoassays in various formats such as radioimmunoassay (RIA), chemiluminescence- and fluorescence-immunoassays, enzyme immunoassay (EIA), enzyme-linked immunoassays (ELISA), luminex-based bead arrays, protein microarray assays, and rapid test formats such as immunochromatographic strip tests, and Selected/Multiple reaction monitoring (SRM/MRM). The immunoassay may be a homogenous or heterogeneous assay, competitive or non-competitive. Examples of other methods for analysis of proteins include spectrometry, mass spectrometry, Matrix Assisted Laser Desorption/Ionization Time-of-Flight (MALDI-TOF) Mass Spectrometry, microscopy, northern blot, isoelectric focussing, SDS-PAGE, PCR, quantitative RT-PCR, gel electrophoresis, DNA microarray, protein sequencing, proteome analysis, and antibody microarray, or combinations thereof.

In an aspect, the fetal analyte is a fetal nucleic acid. In an aspect, a method is provided for detecting and/or isolating fetal nucleic acids from a sample comprising fetal cells, the method comprising introducing the sample into a microfluidic system that allows (i) separation and isolation of fetal cells in the sample; (ii) lysis of the isolated fetal cells, (iii) detection and/or isolation of fetal nucleic acids from the lysed fetal cells, and (iv) optionally analysis of the fetal nucleic acids. The microfluidic system may also comprise culturing of cells in the sample to enrich for fetal cells.

A fetal nucleic acid may be DNA (for example, genomic, mitochondrial, and complementary cDNA from RNA), or RNA (for example, rRNA, mRNA and miRNA). In an aspect, the fetal nucleic acids are nucleotides, oligonucleotides, DNAs, RNAs, or DNA-RNA hybrids. In an embodiment, the fetal nucleic acids are DNAs, in particular, double-stranded DNAs, single-stranded DNAs, multi-stranded DNAs, complementary DNAs, genomic DNAs or non-coding DNAs. In an embodiment, the fetal nucleic acids are RNAs, in particular, messenger RNAs (mRNAs), microRNAs (miRNAs), small nucleolar RNAs (snoRNAs), ribosomal RNAs (rRNAs), transfer RNAs (tRNAs), small interfering RNAs (siRNAs), heterogeneous nuclear RNAs (hnRNAs), or small hairpin RNAs (shRNAs).

The methods and systems disclosed herein may be used for detecting the presence or absence of a target sequence, detection of polymorphisms, single-polynucleotide polymorphism analysis, haplotype analysis, amplification of a sequence for sequence identification, gene expression analysis, quantification of nucleic acids, analysis as well as other applications apparent to one skilled in the art.

In an embodiment, the fetal analyte, in particular, nucleic acid, fetal protein or growth factor, is associated with a prenatal condition.

In an embodiment, a method is provided for detecting or diagnosing a prenatal condition in a sample, in particular an endocervical sample, comprising: (a) introducing the sample into a microfluidic system of the disclosure to separate, isolate and lyse fetal cells in the sample; (b) isolating a fetal protein from the lysed fetal cells; (c) analyzing the fetal protein: and (c) detecting or diagnosing a prenatal condition wherein the presence or absence of a specific fetal protein is indicative of the prenatal condition.

In an embodiment, a method is provided for detecting or diagnosing a prenatal condition in a sample, in particular an endocervical sample, comprising: (a) introducing the sample onto a microfluidic system to separate, isolate and lyse fetal cells in the sample; (b) isolating a fetal nucleic acid from the lysed fetal cells; (c) analyzing the fetal nucleic acid: and (c) detecting or diagnosing a prenatal condition wherein the presence or absence of a specific fetal nucleic acid is indicative of the prenatal condition.

In an embodiment, the disclosure provides a method for diagnosing a prenatal condition in an endocervical sample comprising introducing the sample onto a microfluidic system that allows (i) culturing of cells in the sample to enrich for fetal cells, (ii) separation and isolation of the enriched fetal cells, (iii) lysis of the isolated fetal cells, (iv) isolation of fetal nucleic acids from the lysed fetal cells, and (iv) analysis of the fetal nucleic acids.

A method or system of the disclosure detecting and/or isolating fetal nucleic acids may comprise analyzing the fetal nucleic acids for fetal-specific nucleotide sequences. In an embodiment, the fetal-specific nucleotide sequence is a Y-chromosome sequence.

In aspects, the microfluidic system comprises a microfluidic device and elements to separate and isolate fetal cells and/or maternal cells from other cells in a sample, in particular an endocervical sample, such elements comprising, chosen from, selected from, or selected from the group consisting of binding agents that bind one, two or more fetal cell-specific markers and/or maternal cell-specific markers. In a particular embodiment, the fetal cell-specific markers may comprise, be chosen from or be selected from the group consisting of Fetal Cell Marker 1, Fetal Cell Marker 2, 5T4, HLA-G, CD227, β subunit of chorionic gonadotropin (β-CG), placental lactogen, cytokeratin 7, placental alkaline phosphatase, NDOG1, PSG1, PSG9, MMP14, MCAM, KCNQ4, CLDN6, F3, PEG10, FLT1, CBG,GCM1, GPA, CD45, EGFR, APOB, CD71, CD36, CD34, HbF, FB3-2, H3-3, HAE 9, FB3-2, HBE, APOC3, AMBP, CPB2, ITIH1, APOH, HPX, AHSG, APOB, BPG, carbonic anhydrase (CA), and thymidine kinase. In an embodiment, the maternal cell-specific markers comprise, are chosen from, are selected from, or selected from the group consisting of CD90, CD73, CD44, CD105, and CD29. The binding agents may be labelled with a detectable label as disclosed herein.

A method or system disclosed herein comprising detecting or isolating fetal nucleic acids may further comprise amplifying fetal nucleic acids prior to, or simultaneous with the isolation and/or analysis of the nucleic acids, or subsequent to isolation of the nucleic acids. Amplified nucleic acids may be detected and then pooled for analysis, pooled for subsequent detection and analysis, or detected and not subsequently pooled.

In an embodiment, a system, method or kit disclosed herein comprises amplification reagents necessary for amplifying desired fetal nucleic acids. Amplification reagents may be selected based on the amplification method but can include primers, polymerase, reverse transcriptase, nucleotides, cofactors, metal ions, buffers and similar reagents.

In an embodiment, amplification is carried out in a system of the disclosure wherein the amplification reagents are provided by prepositioning the reagents in the system, by combining the reagents with the fetal analyte, by a combination of both, or by any other suitable method.

Amplicons of fetal nucleic acids may be generated using methods known in the art [see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)) for a discussion of known amplification methods]. Illustrative non-limiting examples of nucleic acid amplification methods include, but are not limited to, Polymerase Chain Reaction (PCR) [see, for example, Dieffenbach and Dvksler, 1995, PCR Primer: A Laboratory Manuel. CSHL press. Cold Spring Harbor, USA; U.S. Pat. Nos. 4,683,195, 4,683,202 and 4,800,159; Mullis et al., Meth. Enzymol. 155: 335 (1987); and, Murakawa et al., DNA 7: 287 (1988)]; reverse transcription polymerase chain reaction (RT-PCR); strand displacement amplification (SDA) [see for example, Walker, G. et al., Proc. Natl. Acad. Sci. USA 89: 392-396 (1992); U.S. Pat. Nos. 5,270,184 and 5,455,166; European Pat. No. 0684315]; transcription mediated amplification (TMA) (see for example, U.S. Pat. Nos. 5,480,784, 5,399,491 and 5,824,518 and Published US Application No. 20060046265); nucleic acid sequence based amplification (NASBA) [see for example, Sooknanan and Malek, 1995, Biotechnology 13:563; U.S. Pat. No. 5,130, 238; Lizardi et al., BioTechnol. 6: 1197 (1988); Kwoh et al., Proc. Natl. Acad. Sci. USA 86:1173 (1989)]; SPIA® [Nugen Technologies, San Carlos, Calif., U.S. Pat. No. 6,251,639, WO 02/72772 and US 20030017591]; the ligase chain reaction (LCR) [see for example, Wu and Wallace, 1989, Genomics 4:560; Weiss, R., Science 254: 1292 (1991), and Landegren et al, 1988, Science 241:1077]; and, self-sustained sequence replication [see for example, Guatelli et al, 1990 Proc Nat Acad Sci USA 87:1874].

Amplicons and non-amplified nucleic acids may be analyzed (i.e., detected, quantified, sequenced and the like) using routine methods known in the art. Examples of methods include, without limitation, mass detection of mass modified amplicons (e.g., matrix-assisted laser desorption ionization (MALDI) mass spectrometry and electrospray (ES) mass spectrometry), a primer extension method (see for example, iPLEX™; Sequenom, Inc.), microsequencing methods, ligase chain reaction, ligase sequence determination methods (see for example, U.S. Pat. Nos. 5,679,524 and 5,952,174, and WO 01/27326), mismatch sequence determination methods (see for example, U.S. Pat. Nos. 5,851,770; 5,958,692; 6,110,684; and 6,183, 958), direct DNA sequencing, restriction fragment length polymorphism, allele specific oligonucleotide analysis, methylation-specific PCR, pyrosequencing analysis, acycloprime analysis, reverse dot blot, GeneChip microarrays, Dynamic allele-specific hybridization, Peptide nucleic acid (PNA) and locked nucleic acids (LNA) probes, TaqMan™, Molecular Beacons, intercalating dye (for example, SYBR™, Pico Green (Molecular Probes, Inc., Eugene, Oreg.), ethidium bromide), fluorescence resonance energy transfer (FRET) based systems, AlphaScreen (Perkin Elmer), SNPstream™ (Beckman Coulter), genetic bit analysis (GBA), multiplex minisequencing, SNaPshot, GOOD assay, microarray miniseq, arrayed primer extension (APEX), microarray primer extension (e.g., microarray sequence determination methods), Tag arrays, Coded microspheres, Template-directed incorporation (TDI), fluorescence polarization, colorimetric oligonucleotide ligation assay (OLA), Sequence-coded OLA, microarray ligation, Padlock probes, Invader assays, hybridization methods, conventional dot blot analyses, single strand conformational polymorphism analysis (SSCP) (see for example, Orita et al., Proc. Natl. Acad. Sci. U.S.A. 86: 27776-2770 (1989)), denaturing gradient gel electrophoresis (DGGE), heteroduplex analysis, mismatch cleavage detection, and cloning and sequencing, electrophoresis, hybridization probes and quantitative real time polymerase chain reaction (QRT-PCR), digital PCR, nanopore sequencing, chips, closed-tube methods for detection and quantification of alleles or paralogs (see for example, Turner et al. BMC Medical Genetics (2015) 16:115).

A system of the disclosure may be used in combination with a sequence analysis apparatus or sequence analysis component(s), including without limitation, the Illumina Genomic Analyzer (or Solexa platform), the SOLID System (Applied Biosystems), the Helicos True Single Molecule DNA sequencing platform (Harris T D et al. 2008 Science, 320, 106-109), the SMRT™ system of Pacific Biosciences, or a nanopore sequencing platform (Soni G V and Meller A. 2007 Clin Chem 53: 1996-2001).

The methods of the disclosure can be used as a clinical laboratory service. In an aspect, the methods include a sample collection device capable of obtaining a sample, for example an endocervical sample, from a subject.

In an aspect, the disclosure provides a kit comprising a diagnostic device comprising a microfluidic system of the disclosure for isolating fetal cells and/or fetal analytes from a sample, in particular an endocervical sample, wherein the system allows separation of the fetal cells, lysis of the lysed fetal cells, and optionally detection or isolation of fetal analytes. The kit optionally comprises components for culturing of cells in the sample to enrich for fetal cells. In an embodiment, the kit comprises binding agents. In an embodiment, the kit comprises imaging agents.

In an embodiment, the disclosure provides a diagnostic kit comprising (a) a diagnostic device comprising a digital microfluidic system for separating and isolating fetal nucleic acids from an endocervical sample wherein the system allows culturing of cells in the sample to enrich for fetal cells, separation of the enriched fetal cells, lysis of the separated fetal cells, and optionally isolation of fetal analytes, wherein the system comprises binding agents that bind to one, two or more fetal-cell specific markers and/or maternal cell-specific markers. In a particular embodiment, the fetal cell-specific markers comprise, are chosen from or selected from the group consisting of Fetal Cell Marker 1, Fetal Cell Marker 2, 5T4, HLA-G, CD227, β subunit of chorionic gonadotropin (β-CG), placental lactogen, cytokeratin 7, placental alkaline phosphatase, NDOG1, PSG1, PSG9, MMP14, MCAM, KCNQ4, CLDN6 and F3, facilitating separation of fetal cells. In a particular embodiment, the maternal cell-specific markers comprise, are chosen from or selected from the group consisting of CD90, CD73, CD44, CD105, and CD29. The binding agents may be labelled with a detectable label disclosed herein.

A diagnostic kit may additionally comprise a sample collection device capable of obtaining an endocervical sample from a subject. A diagnostic kit may additionally comprise reagents for amplifying fetal nucleic acids.

A microfluidic device or system in the method and kits of the disclosure relating to fetal cells and fetal analytes is preferably a microfluidic device or system disclosed herein, however, it will be appreciated by those skilled in the art that other suitable microfluidic devices or systems can be utilized. (See for example, Wu, J et al, Analyst. 2017 Jan. 26; 142(3):421-441; Shields C W et al, Cytometry B Clin Cytom. 2017 March; 92(2):115-125; Shields et al, Lab Chip. 2015 Mar. 7; 15(5):1230-49 for a description of microfluidic devices and methods).

In an aspect, the disclosure relates to the use of a DMF method for identification and isolation of fetal cells and/or fetal analytes within a sample. In another aspect the disclosure relates to a method for detecting and/or isolating fetal cells and/or fetal analytes from a sample. In embodiments, the sample comprises fetal cells and maternal cells. In embodiments, the sample is an endocervical or cervical mucosal sample. In embodiments, the sample is an endocervical or cervical mucosal sample from a pregnant subject.

In embodiments, the method comprises:
(a) loading the sample on at least one hydrophilic site of a digital microfluidic device thereby forming a virtual microwell at each of the at least one hydrophilic site;
(b) immobilizing the cells on the at least one site;
(c) selecting at least one immobilized fetal cell;
(d) lysing the at least one selected fetal cell using a pulsed laser source to produce lysate within its corresponding virtual microwell, wherein the lysate comprises the analytes;
(e) displacing a droplet of liquid to the corresponding virtual microwell for collecting the lysate; and
(f) moving the droplet containing the lysate from the corresponding virtual microwell to a designated site, and optionally detecting and/or isolating analytes in the lysate.

The digital microfluidic device generally comprises an imaging system including a stage for receiving the digital microfluidic device. The imaging system includes an imaging module for identifying the selected fetal cell and the pulsed laser source.

In an embodiment, cells are immobilized in (b) by culturing the cells in the sample to thereby induce cell adhesion on the at least one hydrophilic site to produce adhered cells, and at least one adhered fetal cell is selected in (c).

Positive and/or negative selection or morphological characteristics as disclosed herein or known in the art may be used to select an immobilized fetal cell in (c).

In an embodiment, the method further comprises generating a map of locations of the immobilized (in particular adhered cells), and wherein the step of selecting the at least one immobilized (in particular adhered cell) includes selecting the at least one cell from the map.

In another embodiment, the method further comprises immunocytochemically labelling cells in the sample or labelling adherent cells, and optionally further comprises fixing the cells.

In another embodiment, the method further comprises:
(i) moving the digital microfluidic device along horizontal axes and a vertical axis for positioning the digital microfluidic device for lysing another at least one selected cell from immobilized cells (in particular adhered cells);
(ii) lysing the other at least one selected cell using the pulsed laser source to produce another lysate within corresponding virtual microwell;
(iii) displacing another droplet of liquid to the corresponding virtual microwell for collecting the other lysate; and
(iv) moving the other droplet containing the other lysate from the corresponding virtual microwell to a designated site.

In another embodiment, the method further comprises introducing the sample containing the cells at an initial site and displacing the sample to the at least one hydrophilic site.

In an embodiment, the at least one hydrophilic site is a plurality of hydrophilic sites, and the method comprises:
(i) moving droplets to said plurality of hydrophilic sites,
(ii) selecting of cells to be lysed at each of said plurality of hydrophilic sites,
(iii) selecting a first hydrophilic site to illuminate the selected cell at that hydrophilic site,
(iv) moving the stage to move the digital microfluidic device sequentially to bring each of the hydrophilic sites into a field of view of the pulsed laser source to lyse the selected cell to produce lysate at each hydrophilic site, and
(v) collecting the lysate at each hydrophilic site, and optionally calculating a shortest distance travelled by the stage to bring each of the plurality of hydrophilic sites into the field of view of the pulsed laser source sequentially.

In an embodiment, the selected fetal cell is a plurality of fetal cells and the method comprises identifying a sequence of selected fetal cells to be lysed to minimize a time to perform the lysing on all selected fetal cells, and wherein the plurality of selected fetal cells is within one field of view, or a plurality of field of views, or within a plurality of hydrophilic sites.

In embodiments, the pulsed laser source is a nanosecond-pulsed laser. In a particular embodiment, the pulsed laser source is a nanosecond-pulsed laser delivering pulses of at least 1 µJ, more particularly an Nd-based laser. In embodiments, the nanosecond-pulsed laser produces a pulsed-laser beam within the visible spectrum. In embodiments, the pulsed laser source is a Q-switching laser.

In an embodiment, the method further comprises performing on chip analysis of the lysate at the designated site.

In an embodiment, the method further comprises collecting the droplet containing the lysate from the designated site for off-chip analysis. Analysis of the lysate, in particular fetal analytes, may be performed using the methods disclosed herein or known in the art.

The following non-limiting example is only an example of the use of the system and methods of the present invention.

EXAMPLE

Prenatal Genetic Diagnostic Testing Using DMF/Laser-Microbeam Lysis

The system and method of the present disclosure were used with trophoblast cells from a cervical mucosa sample (CMS). The trophoblast cells, which were adherent and embedded within a sticky, viscous mucous, were not suitable for flow cytometry or microchannels.

Figure 10:
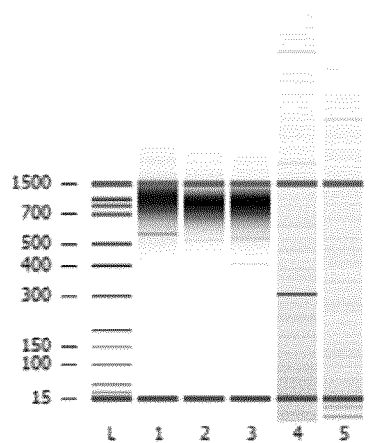
FIG. 10 shows A) an electropheorgram of on-chip laser lysed cells showing size of DNA and B) QF-PCR of the laser lysed cells according to an embodiment of the present invention C) Next generation sequencing of the laser lysed cells according to an embodiment of the present disclosure.
Figure 10:
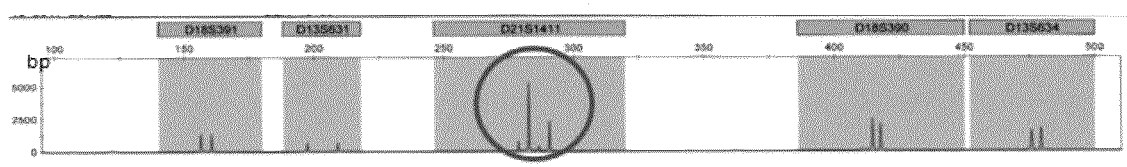
Figure 10:
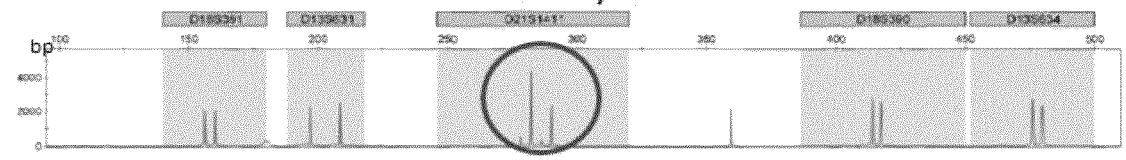
Figure 10:
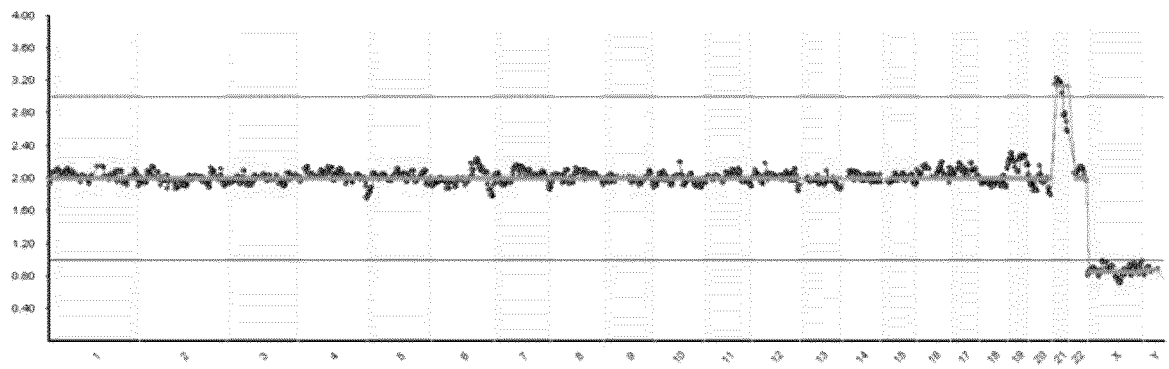

CMS samples were loaded onto a DMF device, where they were seeded and cultured. The samples were stained with markers to identify the fetal cells. After incubation, the media was exchanged, and cells were laser lysed and the lysate was collected for off-chip whole-genome amplification and genotyping. As shown in FIG. 10B the CVS control sample (upper panel) and the matched laser lysed fetal cell sample (lower panel) show the same pattern of heterozygotic alleles by QF-PCR. As show by the circled alleles this same is trisomy 21 positive. FIG. 10C shows genetic analysis of the same laser lysed fetal cell sample using next generation sequencing for analysis and it shows the same trisomy 21 result. The performed steps were as follows:

Cervical Mucousal Sample Preparation (Example of a Specific Method to Generate Single Cell Solution)
1) A cervical mucosal sample is collected by cytobrush;
2) Sample is stored up to 48 hours at 4° C. in 40 ml PBS plus 10 ml AmnioMax media and 0.1 to 5 mM (final) sodium bicarbonate;
3) Sample is warmed to RT and n-acetylcysteine is added to sample to reach between 25 uM and 500 mM.
4) Sample is incubated at 37° C. for 30 to 60 minutes with agitation.
5) Sample is centrifuged for 10 minutes at 300×g at RT.
6) Supernatant is taken down to 10 ml.
7) 15 ml of 0.25% trypsin-EDTA is added.
8) Sample is incubated at 37° C. for 10 to 30 min with agitation.
9) Sample is centrifuged for 10 min at 300×g at RT.

10) Supernatant is removed and sample is resuspended in 500 uL of AmnioMax with 0.05% pluronic f-68.
11) Sampled is transferred to 1.5 ml tube and centrifuge 300×g for 10 min at RT.
12) Sampled is resuspended in 200 uL of AmnioMax with 0.05% pluronic f-68.

Sample Manipulation

13) A DMF device with a top plate containing hydrophilic sites for cell cultures is assembled.
14) Cytobrush cell sample mixture is loaded onto the DMF device and into virtual microwells.
15) The loaded cell sample is incubated overnight at 37 C and 5% $CO_2$ in a humidified flask within the incubator.
16) Cells are fixed using a crosslinking or denaturing fixative such as 4% paraformaldehyde, Clarke's solution, HOPE, ethanol, etc.
17) Immunocytochemical labeling using standard staining and labelling methods is performed using two or more fetal cell markers (markers including but are not limited to 5T4, HLA-G, CD227, cytokeratin 7, NDOG1, PSG1, MMP14, MCAM, KCNQ4, CLDN6, and F3).
18) The DMF device is imaged by tilting microscopy or array scanner. For tilting microscopy the fully assembled device is imaged directly. For the array scanner the device is disassembled and the top plate is washed with water twice and air dried for imaging.
19) Labelled cells are visualized using Cellprofiler to determine fetal cells based on staining pattern of the two fetal cell markers as well as cell size and shape.
20) A map of locations of the fetal cells in the virtual microwells is generated
21) Reassemble the DMF device for DMF-LCL if read on the array scanner.
22) Lyse the fetal cells into PBS (200 µs laser pump pulse, 0-20 µs Q-switch delay)
23) Move PBS droplet to lysis location to collect fetal cell lysate.
24) Move droplet with fetal cell lysate to reservoir.
25) Collect fetal cell lysate from reservoir to use for whole genome amplification (WGA).
26) Run WGA on fetal cell lysate.
27) Run standard prenatal genetic test on the cDNA from the WGA. These tests can be QF-PCR, aCGH (array comparative genomic hybridization), NGS, etc.

Specific Methods of Cell Loading and Analysis with Laser Cell Lysis U87-GFP and B16-tdTomato Cell Protocol 1) Assemble top and bottom plate of DMF device
2) Generate single cell suspension of U87-GFP and/or B16-tdTomato cells in DMEM plus 10% FBS, 1% P/S and 0.05% pluronic F-68
3) Load U87-GFP and/or B16-tdTomato cells into DMF device
4) Culture U87-GFP and/or B16-tdTomato cells on device at 37° C. and 5% $CO_2$ in a humidified flask within the incubator.
5) Replace media with PBS
6) Laser lyse cells
7) Collect cell contents CVS Samples 1) Assemble top and bottom plate of DMF device
2) Replace media on the CVS sample with AmnioMax plus 0.05% pluronic F-68
3) Load CVS sample into DMF device
4) Culture CVS sample on device at 37° C. and 5% $CO_2$ in a humidified flask within the incubator.
5) Replace media with PBS
6) Run whole genome amplification (WGA) on fetal cell lysate.
7) Run standard prenatal genetic test on the cDNA from the WGA. These tests can be QF-PCR, aCGH (array comparative genomic hybridization), NGS, etc.

The present invention is not to be limited in scope by the specific embodiments described herein, since such embodiments are intended as but single illustrations of one aspect of the invention and any functionally equivalent embodiments are within the scope of this invention. Indeed, various modifications of the invention in addition to those shown and described herein will become apparent to those skilled in the art from the foregoing description and accompanying drawings. Such modifications are intended to fall within the scope of the appended claims.

All publications, patents and patent applications referred to herein are incorporated by reference in their entirety to the same extent as if each individual publication, patent or patent application was specifically and individually indicated to be incorporated by reference in its entirety. All publications, patents and patent applications mentioned herein are incorporated herein by reference for the purpose of describing and disclosing the methodologies, reagents, etc. which are reported therein which might be used in connection with the invention. Nothing herein is to be construed as an admission that the invention is not entitled to antedate such disclosure by virtue of prior invention.

REFERENCES

1. Tang, D. G., Understanding cancer stem cell heterogeneity and plasticity. Cell Res, 2012. 22(3): p. 457-72.
2. Graf, T. and M. Stadtfeld, Heterogeneity of embryonic and adult stem cells. Cell Stem Cell, 2008. 3(5): p. 480-3.
3. Lecault, V., et al., High-throughput analysis of single hematopoietic stem cell proliferation in microfluidic cell culture arrays. Nat Methods, 2011. 8(7): p. 581-6.
4. Lecault, V., et al., Microfluidic single cell analysis: from promise to practice. Curr Opin Chem Biol, 2012. 16(3-4): p. 381-90.
5. Macaulay, I. C., et al., G&T-seq: parallel sequencing of single-cell genomes and transcriptomes. Nat Methods, 2015. 12(6): p. 519-22.
6. Macaulay, I. C. and T. Voet, Single cell genomics: advances and future perspectives. PLoS Genet, 2014. 10(1): p. e1004126.
7. Macosko, Evan Z., et al., Highly Parallel Genome-wide Expression Profiling of Individual Cells Using Nanoliter Droplets. Cell, 2015. 161(5): p. 1202-1214.
8. Treutlein, B., et al., Reconstructing lineage hierarchies of the distal lung epithelium using single-cell RNA-seq. Nature, 2014. 509(7500): p. 371-375.
9. Kolodziejczyk, A. A., et al., The technology and biology of single-cell RNA sequencing. Mol Cell, 2015. 58(4): p. 610-20.
10. Klein, A. M., et al., Droplet barcoding for single-cell transcriptomics applied to embryonic stem cells. Cell, 2015. 161(5): p. 1187-201.
11. Ng, A. H., et al., Digital microfluidic magnetic separation for particle-based immunoassays. Anal Chem, 2012. 84(20): p. 8805-12.
12. Ng, A. H., et al., Digital microfluidic platform for the detection of rubella infection and immunity: a proof of concept. Clin Chem, 2015. 61(2): p. 420-9.
13. Barbulovic-Nad, I., S. H. Au, and A. R. Wheeler, A microfluidic platform for complete mammalian cell culture. Lab Chip, 2010. 10(12): p. 1536-42.

14. Srigunapalan, S., et al., A digital microfluidic platform for primary cell culture and analysis. *Lab Chip,* 2012. 12(2): p. 369-75.
15. Ng, A. H., et al., Digital microfluidic immunocytochemistry in single cells. *Nat Commun,* 2015. 6: p. 7513.
16. Lai, H. H., et al., Characterization and use of laser-based lysis for cell analysis on-chip. *J R Soc Interface,* 2008. 5 Suppl 2: p. S113-21.
17. Quinto-Su, P. A., et al., Examination of laser microbeam cell lysis in a PDMS microfluidic channel using time-resolved imaging. *Lab Chip,* 2008. 8(3): p. 408-14.
18. Sims, C. E., et al., Laser-micropipet combination for single-cell analysis. *Anal Chem,* 1998. 70(21): p. 4570-7.
19. Eydelnant, I. A., et al., Virtual microwells for digital microfluidic reagent dispensing and cell culture. *Lab Chip,* 2012. 12(4): p. 750-7.
20. Kratschmer, E, et al., Image processing using shape recognition for alignment to damaged registration marks in electron beam lithography. *J. Vac. Sci. Technol., B: Microelectron. Nanometer Struct.—Process., Meas., Phenom. B,* 2009. 27: p. 2563-2568.
21. Held, M and Karp, R M, A Dynamic Programming Approach to Sequencing Problems. *J. Soc. Ind. Appl. Math.* 1962 10(1): p. 196-210.
22. Johnson, D. S.; McGeoch, L. A. (1997). "The Traveling Salesman Problem: A Case Study in Local Optimization". In Aarts, E. H. L.; Lenstra, J. K. Local Search in Combinatorial Optimisation. London: John Wiley and Sons Ltd. pp. 215-310.

The invention claimed is:

1. A system for identifying and targeting individual cells within a plurality of cells contained in a sample for selective extraction of cellular content, comprising:
   a digital microfluidic device comprising a plate patterned to define at least one site configured to receive fluid and form a first droplet of said fluid thereon, and to adhere cells contained in the droplet, said site having an external perimeter and at least a portion of said plate being outside said external perimeter, said digital microfluidic device having a plurality of electrodes for moving droplets across said plate;
   an imaging system including a stage for receiving the digital microfluidic device, the imaging system including:
      an imaging module for imaging a plurality of cells adhered at a site of said at least one site and identifying at least one targeted cell from among the plurality of cells, wherein the plurality of cells further comprises at least one untargeted cell; and
      a pulsed laser source for laser lysing the at least one targeted cell thereby releasing the cell content to produce a lysate in said first droplet; and
   a control system for controlling the pulsed laser source, the imaging system and the digital microfluidic device, the control system being programmed with instructions for coordinating, when the digital microfluidics device is received at the stage:
      dispensing a first fluid droplet containing cells at a first one of said at least one site, to thereby adhere a plurality of said cells at said first one of said at least one site;
      selecting at least one targeted cell to be lysed from the plurality of cells at said first one of said at least one site,
      illuminating the at least one selected targeted cell at said first one of said at least one site by the pulsed laser source to lyse the at least one selected targeted cell to produce lysate;
      dispensing a second fluid droplet at a location on said plate outside of said first one of said at least one site;
      actuating said electrodes to move said second droplet across said plate to said first one of said at least one site;
      actuating said electrodes to move fluid containing the lysate across the plate away from the first site to a location on said plate outside said external perimeter of said site, to separate said fluid containing the lysate from the at least one untargeted cell at said site,
      wherein the at least one untargeted cell remains adhered to the site after the fluid containing the lysate is moved to said location on said plate outside said external perimeter of said site.

2. The system according to claim 1 wherein the at least one site is hydrophilic, partially hydrophilic or become hydrophilic after protein fouling/adsorption from the sample.

3. The system according to claim 1 wherein the digital microfluidic device includes a top plate and a bottom plate defining a space there between, and wherein the at least one site comprises a plurality of sites, each being defined on a surface of at least one of the plates for forming a corresponding virtual microwell, each corresponding virtual microwell having a virtual wall extending from the external perimeter of the respective site between the top and bottom plates, and
   wherein, upon illumination of the at least one selected targeted cell by the pulsed laser source, a plasma bubble is formed in the virtual microwell, and
   wherein upon formation of the plasma bubble, the virtual wall deforms thereby absorbing energy released by the expanding plasma bubble.

4. The system according to claim 1, wherein the at least one site comprises a plurality of sites, and wherein the control system is programmed with instructions for coordinating
   dispensing fluid droplets containing cells at a multiple selected ones of said plurality of sites, to thereby adhere a plurality of said cells at each of said multiple selected ones of said sites;
   selecting, from the cells adhered at said multiple selected ones of said plurality of sites, at least one cell at each of said multiple selected ones of said plurality of sites,
   illuminating with the pulsed laser source the at least one selected cell at each of said multiple selected ones of said plurality of sites, and
   moving of the stage to move the digital microfluidic device to sequentially bring each of the multiple selected ones of said plurality of sites into a field of view of the pulsed laser source to lyse the at least one selected cell to produce lysate in a droplet at each of said multiple selected ones of said plurality of sites.

5. The system according to claim 4 wherein the control system is programmed for calculating a shortest distance travelled by the stage to bring sequentially each of the selected sites into the field of view of the pulsed laser.

6. The system according to claim 1 wherein the at least one selected targeted cell is a plurality of selected targeted cells and said at least one site comprises a plurality of sites, the control system being programmed for identifying a sequence of selected targeted cells to be lysed to minimize a time to perform the coordinating steps, and
wherein the plurality of selected targeted cells is within one field of view, or a plurality of field of views, or within multiple ones of said plurality of sites.

7. The system according to claim 6 wherein the sequence of selected targeted cells is based on a shortest path between the plurality of selected targeted cells.

8. The system according to claim 1 wherein the imaging system includes a translation mechanism for displacement of the stage, the translation mechanism being controlled by the control system.

9. The system according to claim 1 wherein the control system includes a droplet control means for actuating said plurality of electrodes to control displacement of droplets of fluid from a fluid reservoir towards the at least one site.

10. The system according to claim 1 wherein the pulsed laser source is a nanosecond-pulsed laser.

11. The system according to claim 1 wherein the pulsed laser source is a nanosecond-pulsed laser delivering pulses of at least 1 µJ.

12. The system according to claim 1 wherein the pulsed laser source is a Q-switched laser.

13. The system according to claim 10 wherein the nanosecond-pulsed laser is a Nd-based laser.

14. The system according to claim 10, wherein the nanosecond-pulsed laser produces a pulsed-laser beam within the visible spectrum.

15. The system according to claim 2 wherein the digital microfluidic device includes a top plate and a bottom plate defining a space there between, and wherein the at least one site comprises a plurality of sites, each being defined on a surface of at least one of the plates for forming a corresponding virtual microwell, each corresponding virtual microwell having a virtual wall extending from the external perimeter of the site between the top and bottom plates, and
wherein, upon illumination of the at least one selected targeted cell by the pulsed laser source, a plasma bubble is formed in the virtual microwell, and
wherein upon formation of the plasma bubble, the virtual wall deforms thereby absorbing energy released by the expanding plasma bubble.

16. The system according to claim 2, wherein the at least one site comprises a plurality of sites, and wherein the control system is programmed with instructions for coordinating
dispensing fluid droplets containing cells at a multiple selected ones of said plurality of sites, to thereby adhere a plurality of said cells at each of said multiple selected ones of said sites;
selecting, from the cells adhered at said multiple selected ones of said plurality of sites, at least one cell at each of said multiple selected ones of said plurality of sites
illuminating with the pulsed laser source the at least one selected cell at each of said multiple selected ones of said plurality of sites, and
moving of the stage to move the digital microfluidic device to sequentially bring each of the multiple selected ones of said plurality of sites into a field of view of the pulsed laser source to lyse the at least one selected cell to produce lysate in a droplet at each of said multiple selected ones of said plurality of sites.

17. The system according to claim 16 wherein the control system is programmed for calculating a shortest distance travelled by the stage to bring sequentially each of the selected sites into the field of view of the pulsed laser.

18. The system according to claim 2 wherein the at least one selected targeted cell is a plurality of selected targeted cells and said at least one site comprises a plurality of sites, the control system being programmed for identifying a sequence of selected targeted cells to be lysed to minimize a time to perform the coordinating steps, and
wherein the plurality of selected targeted cells is within one field of view, or a plurality of field of views, or within multiple ones of said plurality of sites.

19. The system according to claim 18 wherein the sequence of selected targeted cells is based on a shortest path between the plurality of selected targeted cells.

20. The system according to claim 2 wherein the imaging system includes a translation mechanism for displacement of the stage, the translation mechanism being controlled by the control system.

21. The system according to claim 1 wherein the control system is programmed with instructions for coordinating the step of moving the droplet containing the lysate to the designated site by displacing another droplet to the first one of said at least one site.

22. The system according to claim 1 wherein the sample is a suspension of a cell population, said suspension being in a droplet form.

23. The system according to claim 1 wherein the sample is a biopsied tissue or a smear containing a cell population.

24. The system according to claim 1, wherein said plate is a first plate and said digital microfluidic plate further comprises a second plate patterned with said electrodes.

25. The system according to claim 1, wherein said electrodes are patterned on said plate.

26. The system according to claim 1, wherein each of said at least one site is defined by hydrophobic and hydrophilic regions patterned on said plate.

27. The system according to claim 1, wherein said dispensing a first fluid droplet comprises passive dispensing by droplet surface tension.

28. The system according to claim 1, wherein said dispensing a first fluid droplet comprises actuating said plurality of electrodes.

* * * * *